(12) United States Patent
Zhao et al.

(10) Patent No.: US 8,263,062 B2
(45) Date of Patent: *Sep. 11, 2012

(54) MULTI-ARM POLYMER PRODRUGS

(75) Inventors: Xuan Zhao, Dong Cheng District (CN); Michael D. Bentley, Huntsville, AL (US); Zhongxu Ren, Madison, AL (US); Tacey X. Viegas, Madison, AL (US)

(73) Assignee: Nektar Therapeutics, San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/709,800

(22) Filed: Feb. 22, 2010

(65) Prior Publication Data

US 2010/0152414 A1    Jun. 17, 2010

Related U.S. Application Data

(63) Continuation of application No. 10/943,799, filed on Sep. 17, 2004, now Pat. No. 7,744,861.

(60) Provisional application No. 60/503,673, filed on Sep. 17, 2003, provisional application No. 60/584,308, filed on Jun. 30, 2004.

(51) Int. Cl.
*A61K 31/74* (2006.01)
*A61K 47/48* (2006.01)

(52) U.S. Cl. .................................. 424/78.17

(58) Field of Classification Search .......... None
See application file for complete search history.

(56) References Cited

U.S. PATENT DOCUMENTS

| | | |
|---|---|---|
| 5,614,549 A | 3/1997 | Greenwald et al. |
| 5,648,506 A | 7/1997 | Desai et al. |
| 5,681,567 A | 10/1997 | Martinez et al. |
| 5,840,900 A | 11/1998 | Greenwald et al. |
| 5,859,022 A | 1/1999 | Hausheer et al. |
| 5,880,131 A | 3/1999 | Greenwald et al. |
| 5,965,566 A | 10/1999 | Greenwald et al. |
| 6,011,042 A | 1/2000 | Greenwald et al. |
| 6,121,451 A | 9/2000 | Henegar et al. |

(Continued)

FOREIGN PATENT DOCUMENTS

EP    0757049 B1    3/1999

(Continued)

OTHER PUBLICATIONS

Rowinsky, et al., "A phase I and pharmacokinetic study of pegylated camptothecin as a 1-hour infusion every 3 weeks in patients with advanced soild malignancies", J. Clin. Oncol., vol. 21, pp. 148-157 (2003).

(Continued)

*Primary Examiner* — Paul Dickinson
(74) *Attorney, Agent, or Firm* — Susan T. Evans; King & Spalding

(57) ABSTRACT

Provided herein are water-soluble prodrugs. The prodrugs of the invention comprise a water-soluble polymer having three or more arms, at least three of which are covalently attached to an active agent, e.g., a small molecule. The conjugates of the invention provide an optimal balance of polymer size and structure for achieving improved drug loading, since the conjugates of the invention possess three or more active agents releasably attached to a multi-armed water soluble polymer. The prodrugs of the invention are therapeutically effective, and exhibit improved properties in-vivo when compared to unmodified parent drug.

17 Claims, 9 Drawing Sheets

U.S. PATENT DOCUMENTS

| | | | |
|---|---|---|---|
| 6,127,355 | A | 10/2000 | Greenwald et al. |
| 6,153,655 | A | 11/2000 | Martinez et al. |
| 6,194,580 | B1 | 2/2001 | Greenwald et al. |
| 6,395,266 | B1 | 5/2002 | Martinez et al. |
| 6,403,569 | B1 | 6/2002 | Achterrath |
| 6,461,603 | B2 | 10/2002 | Bentley et al. |
| 6,541,508 | B2 | 4/2003 | Ekwuribe et al. |
| 6,608,076 | B1 | 8/2003 | Greenwald et al. |
| 6,756,037 | B2 | 6/2004 | Greenwald et al. |
| 6,777,387 | B2 | 8/2004 | Greenwald et al. |
| 7,744,861 | B2 | 6/2010 | Zhao et al. |
| 2001/0041172 | A1 | 11/2001 | Bentley et al. |
| 2002/0182172 | A1 | 12/2002 | Bentley et al. |
| 2003/0065023 | A1* | 4/2003 | Swindell et al. ............ 514/449 |
| 2003/0105275 | A1 | 6/2003 | Bentley et al. |
| 2004/0037802 | A1 | 2/2004 | Zhao et al. |
| 2004/0058981 | A1 | 3/2004 | Lai et al. |
| 2004/0077595 | A1 | 4/2004 | Cheng et al. |

FOREIGN PATENT DOCUMENTS

| | | |
|---|---|---|
| EP | 0923566 B1 | 10/2003 |
| WO | WO 97/35552 A1 | 9/1997 |
| WO | WO 98/41562 A1 | 9/1998 |
| WO | WO 99/17804 | 4/1999 |
| WO | WO 99/53951 A1 | 10/1999 |
| WO | WO 00/04486 A1 | 11/2000 |
| WO | WO 01/46291 A1 | 6/2001 |
| WO | WO 01/62299 A1 | 8/2001 |
| WO | WO 01/74402 A1 | 10/2001 |
| WO | WO 02/43772 A2 | 6/2002 |
| WO | WO 02/08789 A1 | 11/2002 |
| WO | WO 02/089789 A1 | 11/2002 |
| WO | WO 03/031467 A1 | 4/2003 |
| WO | WO 03/037384 A1 | 5/2003 |
| WO | WO 03/037385 A1 | 5/2003 |

OTHER PUBLICATIONS

Nektar Advanced PEGylation catalog, "Polyethylene glycol and derivatives for advanced PEGylation", pp. 1-30 (2005-2006).

NOF Corporation catalog, "Peg derivatives, phospholipid and drug delivery materials for pharmaceuticals/products and formulations", pp. 1-59 (2006).

NOF Corporation website, "PEGylation and activated PEGs", retrieved from the NOF Corporation website on Dec. 12, 2006, 9 pages (2006).

Polypure Products catalog, 5 pages, Apr. 2005.

Quanta Biodesign Limited catalog. pp. 1-51, Nov. 17, 2005.

Astruc, et al., "Dendritic catalysts and dendrimers in catalysis", Chem. Rev., 101 2991-3023 (2001).

Conover, et al., "Camptothecin delivery systems: enhanced efficacy and tumor accumulation of camptothecin following its conjugation to polyethylene glycol via a glycine linker", Cancer Chemotherapy Pharmacology, 42.(5):407-414 (1998).

Conover, et al., Camptothecin delivery systems: the utility of amino acid spacers for the conjugation of camptotheoin with polyethylene glycol to create prodrugs , Anti-Cancer Drug Qesign, 14(6):499-506 (1999).

Enzon Pharmaceuticals Catalog, "Macromolecular Engineering Technologies", p. 1-14 (2004).

Greenwald et al., "Poly(ethylene glycol) conjugated drugs and prodrugs: a comprehensive review", Critical Reviews in Therapeutic Carrier Systems, 17(2):101-161 (2000).

Nektar Advanced PEGylation Catalog, "Polyethylene Glycol and Derivatives for Advanced PEGylation", pp. 1-21 (2003).

Nektar Advanced PEGylation Catalog, "Polyethylene Glycol and Derivatives for Advanced PEGylation", pp. 1-24 (2004).

NOF Corporation Catalog; "Peg Derivatives, Phospholipid and Drug Delivery Materials for Pharmaceuticals", 1:1-45 (2003).

Omayra, et al., "Polyester Dendritic Systems for Drug Delivery Applications: In Vitro and In Vivo Evaluation", Bioconjugate Chemistry, 13:453-461 (2002).

Polypure Products Catalog, 5 pages, (Apr. 2004).

Quanta Biodesign Catalog, "Labeling, Derivatization and Crosslinking Reagents for Biological and Related Materials with dPEG", pp. 1-38, (Mar. 12, 2004).

Quanta Biodesign Catalog, "Labeling, Derivatization and Crosslinking Reagents for Biological and Related Materials with dPEG", pp. 1-31, (Nov. 5, 2004).

Shearwater Polymers, Inc., Catalog, "Functionalized Biocompatible Polymers for Research: Polyethylene Glycol and Derivatives", pp. 2-49 (Mar. 1995).

Shearwater Polymers, Inc., Catalog, "Functionalized Biocompatible Polymers for Research and Pharmaceuticals: Polyethylene Glycol and Derivatives", pp. 2-53 (1997-1998).

Shearwater Polymers, Inc., Catalog, "Functionalized Biocompatibie Polymers for Research and Pharmaceuticals: Polyethylene Glycol and Derivatives", pp. 2-50 (2000).

Shearwater Corporation, "Polyethylene Glycol and Derivatives for Biomedical Applications", pp. 1-17 (2001).

Warnecke, et al., "Maleimide-oligo(ethylene glycol) derivatives of carnptothecin as albumin-binding prodrugs: synthesis and antitumor efficacy", Bioconjugate Chemistry, 14:377-387 (2003).

Zalispky, et al., "Attachment of drugs to polyethylene glycols," Eur. J. Polym. J., 19(12).1177-1183 (1983).

International Search Report for PCT application PCT/US2004/030720 filed Sep. 17, 2004, International Search Report dated Oct. 17, 2005, 24 pages (2005).

Polypure Products Catalog, 5 pages, (Apr. 2005).

Written Opinion for PCT application PCT/US2004/030720 filed Sep. 17, 2004, Written Opinion dated Oct. 17, 2005, 24 pages (2005).

* cited by examiner

MULTI-ARM POLYMER PRODRUGS

CROSS REFERENCE TO RELATED APPLICATIONS

This application is a continuation of U.S. patent application Ser. No. 10/943,799, filed Sep. 17, 2004, which claims the benefit of priority to U.S. Provisional Application No. 60/503,673, filed Sep. 17, 2003, and to U.S. Provisional Application No. 60/584,308, filed Jun. 30, 2004, the contents each of which is incorporated herein by reference in its entirety.

FIELD

This invention relates to multi-arm, water-soluble polymer drug conjugates, and in particular, to polymer-based prodrugs, and to methods for preparing, formulating and administering compositions comprising such prodrugs.

BACKGROUND

Over the years, numerous methods have been proposed for improving the delivery of biologically active agents. Challenges associated with the formulation and delivery of pharmaceutical agents can include poor aqueous solubility of the pharmaceutical agent, toxicity, low bioavailability, instability, and rapid in-vivo degradation, to name just a few. Although many approaches have been devised for improving the delivery of pharmaceutical agents, no single approach is without its drawbacks. For instance, commonly employed drug delivery approaches aimed at solving or at least ameliorating one or more of these problems include drug encapsulation, such as in a liposome, polymer matrix, or unimolecular micelle, covalent attachment to a water-soluble polymer such as polyethylene glycol, use of gene targeting agents, and the like.

In looking more closely at some of these approaches, liposome encapsulation is often plagued by low efficiencies of drug loading, resulting in an oftentimes inefficient and cost ineffective process. Moreover, the release rate of the active agent in a liposomal formulation depends upon dissolution or disintegration of the liposome, or diffusion of the active agent through the liposomal layers, thereby limiting the practical availability of the active agent to the biological system. In addition, liposomal formulations are generally restricted to lipid soluble drugs. Polymer matrix-based formulations can suffer from similar shortcomings, such as the inability to well-characterize such drug delivery systems, particular those that are cross-linked, and the variable release rates associated with active agents that must diffuse out of a hydrolytically degradable polymer matrix. In comparison, conjugation of an active agent to a polymer such as polyethylene glycol offers a more well-defined alternative, since the conjugate itself is often although not necessarily well-characterized, particularly in the case of site-specific attachment of the polymer to the active agent. However, protein-based compositions containing mixtures of positional isomers varying in both the site(s) and number of polymer chains attached to a particular protein are not uncommon. This can lead to problems with reproducibly preparing such compositions.

While modification of therapeutic proteins for the purpose of improving their pharmaceutical utility is perhaps one of the most common applications of PEGylation, PEGylation has also been used, albeit to a limited degree, to improve the bioavailability and ease of formulation of small molecule therapeutics having poor aqueous solubilities. For instance, water-soluble polymers such as PEG have been covalently attached to artilinic acid to improve its aqueous solubility (Bentley, et al., U.S. Pat. No. 6,461,603). Similarly, PEG has been covalently attached to triazine-based compounds such as trimelamol to improve their solubility in water and enhance their chemical stability (Bentley, et al., WO 02/043772). Covalent attachment of PEG to bisindolyl maleimides has been employed to improve poor bioavailability of such compounds due to low aqueous solubility (Bentley, et al., WO 03/037384). Prodrugs of camptothecin having one or two molecules of camptothecin covalently attached to a linear polyethylene glycol have similarly been prepared (Greenwald, et al, U.S. Pat. No. 5,880,131).

Camptothecin (often abbreviated as "CPT") is a phytotoxic alkaloid first isolated from the wood and bark of *Camptotheca acuminata* (Nyssaceae), and has been shown to exhibit antitumor activity. The compound has a pentacyclic ring system with an asymmetric center in lactone ring E with a 20 S configuration. The pentacyclic ring system includes a pyrrolo [3,4-b]quinoline (rings A, B and C), a conjugated pyridone (ring D), and a six-membered lactone (ring E) with a 20-hydroxyl group. Due to its insolubility in water, camptothecin was initially evaluated clinically in the form of a water-soluble carboxylate salt having the lactone ring open to form the sodium salt. The sodium salt, although exhibiting much improved water solubility in comparison to camptothecin itself, produced severe toxicity and demonstrated very little in vivo anticancer activity, thus demonstrating the undesirability of this approach.

It was later discovered that camptothecin and many of its derivatives inhibit topoisomerase, an enzyme that is required for swiveling and relaxation of DNA during molecular events such as replication and transcription. Camptothecin stabilizes and forms a reversible enzyme-camptothecin-DNA ternary complex. The formation of the cleavable complex specifically prevents the reunion step of the breakage/union cycle of the topoisomerase reaction. Topoisomerase I inhibitors are also known to be useful in the treatment of HIV.

In an effort to address the poor aqueous solubility associated with camptothecin and many of its derivatives, a number of synthetic efforts have been directed to derivatizing the A-ring and/or B-ring or esterifying the 20-hydroxyl to improve water-solubility while maintaining cytotoxic activity. For example, topotecan (9-dimethylaminomethyl-10-hydroxy CPT) and irinotecan (7-ethyl-10[4-(1-piperidino)-1-piperidino]carbonyloxy CPT), otherwise known as CPT-11, are two water-soluble CPT derivatives that have shown clinically useful activity. Conjugation of certain camptothecin derivatives, such as 10-hydroxycamptothecin and 11-hydroxycamptothecin, to a linear poly(ethylene glycol) molecule via an ester linkage has been described as a means to form water soluble prodrugs (Greenwald, et al., U.S. Pat. No. 6,011,042).

The clinical effectiveness of many small molecule therapeutics, and oncolytics in particular, is limited by several factors. For instance, irinotecan and other camptothecin derivatives undergo an undesirable hydrolysis of the E-ring lactone under alkaline conditions. Additionally, administration of irinotecan causes a number of troubling side effects, including leukopenia and diarrhea. Due to its severe diarrheal side-effect, the dose of irinotecan that can be administered in its conventional, unmodified form is extremely limited, thus hampering the efficacy of this drug and others of this type.

These associated side effects, when severe, can be sufficient to arrest further development of such drugs as promising therapeutics. Additional challenges facing small molecules include high clearance rates, and in the instance of anticancer agents, minimal tumor permeation and residence time. Approaches involving the use of polymer attachment must balance the size of the polymer against the molecular weight of the active agent in order to allow therapeutically effective doses to be delivered. Finally, the synthesis of a modified or drug-delivery enhanced active agent must result in reasonable yields, to make any such approach economically attractive. Thus, there exists a need for new methods for effectively delivering drugs, and in particular small molecule drugs, and even more particularly oncolytics, which can reduce their adverse and often toxic side-effects, whilst simultaneously improving their efficacy and ease of formulation. Specifically, there is a need for improved methods for delivering drugs that possess an optimal balance of bioavailability due to reduced clearance times, bioactivity, and efficacy, coupled with reduced side-effects. The present invention meets those needs.

SUMMARY

In one aspect, the present invention provides water-soluble prodrugs. The prodrugs of the invention comprise a water-soluble polymer having three or more arms, at least three of which are covalently attached to an active agent, e.g., a small molecule. The conjugates of the invention provide an optimal balance of polymer size and structure for achieving improved drug loading, since the conjugates of the invention possess three or more active agents attached, preferably releasably, to a water soluble polymer. In one embodiment, each of the arms of the water soluble polymer possesses an active agent covalently attached thereto, preferably by a hydrolyzable linkage.

In one embodiment, the prodrug conjugate comprises a multi-arm polymer, i.e., having three or more arms, where the conjugate comprises the following generalized structure:

$$R(\text{-}Q\text{-}POLY_1\text{-}X\text{-}D)_q \quad \quad I$$

In structure I, R is an organic radical possessing from about 3 to about 150 carbon atoms, preferably from about 3 to about 50 carbon atoms, and even more preferably from about 3 to about 10 carbon atoms, optionally containing one or more heteroatoms (e.g., O, S, or N). In one embodiment, R possesses a number of carbon atoms selected from the group consisting of 3, 4, 5, 6, 7, 8, 9, and 10. R may be linear or cyclic, and typically, emanating therefrom are at least 3 independent polymer arms each having at least one active agent moiety covalently attached thereto. Looking at the above structure, "q" corresponds to the number of polymer arms emanating from "R".

In structure I, Q is a linker, preferably one that is hydrolytically stable. Typically, Q contains at least one heteroatom such as O, or S, or NH, where the atom proximal to R in Q, when taken together with R, typically represents a residue of the core organic radical R. Illustrative examples are provided below. Generally, Q contains from 1 to about 10 atoms, or from 1 to about 5 atoms. More particularly, Q typically contains one of the following number of atoms: 1, 2, 3, 4, 5, 6, 7, 8, 9, or 10. In a particular embodiment, Q is O, S, or —NH—C(O)—.

In structure I, $POLY_1$ represents a water-soluble and non-peptidic polymer. Representative polymers include poly (alkylene glycol), poly(olefinic alcohol), poly(vinylpyrrolidone), poly(hydroxyalkylmethacrylamide), poly (hydroxyalkylmethacrylate), poly(saccharide), poly(α-hydroxy acid), poly(acrylic acid), poly(vinyl alcohol), polyphosphazene, polyoxazoline, poly(N-acryloylmorpholine), or copolymers or terpolymers thereof. In a particular embodiment of structure I, $POLY_1$ is a polyethylene glycol, preferably a linear polyethylene glycol (i.e., in each arm of the overall multi-arm structure). In yet another embodiment, $POLY_1$ corresponds to the structure, $-(CH_2CH_2O)_n-$, where n ranges from about 10 to about 400, preferably from about 50 to about 350.

In structure I, X is a spacer that comprises a hydrolyzable linkage, where the hydrolyzable linkage is attached directly to the active agent, D. Typically, at least one atom of the hydrolyzable linkage is contained in the active agent, D, in its unmodified form, such that upon hydrolysis of the hydrolyzable linkage comprised within X, the active agent, D, is released. Generally speaking, the spacer, X, has an atom length of from about 4 atoms to about 50 atoms, or more preferably from about 5 atoms to about 25 atoms, or even more preferably from about 5 atoms to about 20 atoms. Representative spacers have a length of from about 5, 6, 7, 8, 9, 10, 11, 12, 13, 14, 15, 16, 17, 18, 19, or about 20 atoms.

In yet another particular embodiment, X possesses the structure: Y-Z, where Y is a spacer fragment covalently attached to Z, a hydrolytically degradable linkage. In certain embodiments, Z itself may not constitute a hydrolytically degradable linkage, however, when taken together with Y, or at least a portion of Y, forms a linkage that is hydrolytically degradable.

In yet a more particular embodiment of the spacer, X, Y has the structure: $-(CR_xR_y)_a-K-(CR_xR_y)_b-(CH_2CH_2O)_c-$, wherein each $R_x$ and $R_y$, in each occurrence, is independently H or an organic radical selected from the group consisting of alkyl, substituted alkyl, alkenyl, substituted alkenyl, alkynyl, substituted alkynyl, aryl, and substituted aryl, a ranges from 0 to 12 (i.e., can be 0, 1, 2, 3, 4, 5, 6, 7, 8, 9, 10, 11, or 12), b ranges from 0 to 12 (i.e., can be 0, 1, 2, 3, 4, 5, 6, 7, 8, 9, 10, 11, or 12), K is selected from —C(O)—, —C(O)NH—, —NH—C(O)—, —O—, —S—, O—C(O)—, C(O)—O—, O—C(O)—O—, O—C(O)—NH—, NH—C(O)—O—, c ranges from 0 to 25, and Z is selected from C(O)—O—, O—C(O)—O—, —O—C(O)—NH—, and NH—C(O)—O—. The particular structure of K and of Z will depend upon the values of each of a, b, and c, such that none of the following linkages result in the overall structure of spacer X, —O—O—, NH—O—, NH—NH—.

Preferably, Y comprises $(CH_2)_a-C(O)NH-(CH_2)_{0,1}-(CH_2CH_2O)_{0-10}$.

In yet another embodiment of the spacer, X, Y has the structure: $-(CR_xR_y)_a-K-(CR_xR_y)_b-(CH_2CH_2NH)_c-$, where the variables have the values previously described. In certain instances, the presence of the short ethylene oxide or ethyl amino fragments in spacer, X, can be useful in achieving good yields during preparation of the prodrug conjugate, since the presence of the linker can help to circumvent problems associated with steric hindrance, due to the multi-armed reactive polymer, the structure of the active agent, or a combination of both. Preferably, c is selected from the group consisting of 0, 1, 2, 3, 4, 5, 6, 7, 8, 9, and 10.

Preferably, $R_x$ and $R_y$ in each occurrence are independently H or lower alkyl. In one embodiment, $R_x$ and $R_y$ are in each occurrence H. In yet another embodiment, a ranges from 0 to 5. In yet another embodiment, b ranges from 0 to 5. In yet another embodiment, c ranges from 0 to 10. In yet another embodiment, K is —C(O)—NH. Any of the embodiments described herein is meant to apply not only to generalized structure I, but also to extend to particular combinations of embodiments.

In yet another embodiment, $R_x$ and $R_y$ in each occurrence are H, a is 1, K is —C(O)—NH, and b is 0 or 1.

Representative examples of X include —CH$_2$—C(O)—NH—CH$_2$—C(O)O— (here, Y corresponds to —CH$_2$—C(O)—NH—CH$_2$— and Z corresponds to —C(O)—O—), and —CH$_2$—C(O)—NH—(CH$_2$CH$_2$O)$_2$—C(O)—O— (here, Y corresponds to —CH$_2$—C(O)—NH—(CH$_2$CH$_2$O)$_2$— and Z corresponds to —C(O)—O—).

Returning now to structure I, D is an active agent moiety, and q (the number of independent polymer arms) ranges from about 3 to about 50. Preferably, q ranges from about 3 to about 25. More preferably, q is from 3 to about 10, and possesses a value of 3, 4, 5, 6, 7, 8, 9, or 10.

In accordance with one embodiment of the invention, the conjugate comprises a polymer having from about 3 to about 25 active agent molecules covalently attached thereto. More particularly, the conjugate comprises a water soluble polymer having 3, 4, 5, 6, 7, 8, 9, 10, 11, 12, 13, 14, 15, 16, 17, 18, 19, 20, 21, 22, 23, 24, or 25 active agent molecules covalently attached thereto. In a further embodiment, the conjugate of the invention has from about 3 to about 8 active agent molecules covalently attached to the water-soluble polymer. Typically, although not necessarily, the number of polymer arms will correspond to the number of active agents covalently attached to the water soluble polymer.

The active agent moiety, D, is an active agent comprising a functional group suitable for covalent attachment to the multi-armed polymer described herein to form a hydrolyzable linkage, such that upon hydrolysis, the active agent is released in its unmodified form.

Preferred active agent moieties include anticancer agents.

In one embodiment, the active agent is a small molecule. In a particular embodiment, the active agent moiety is a small molecule possessing a molecular weight of less than about 1000. In yet additional embodiments, the small molecule drug possesses a molecular weight of less than about 800, or even less than about 750. In yet another embodiment, the small molecule drug possesses a molecular weight of less than about 500 or, in some instances, even less than about 300.

In yet another embodiment, the small molecule is an oncolytic drug having at least one hydroxyl group.

In yet a further embodiment, D represents a camptothecin compound having the structure:

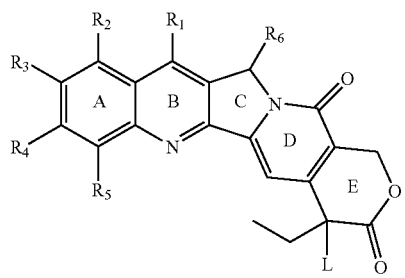

VII wherein R$_1$-R$_5$ are each independently selected from the group consisting of hydrogen; halo; acyl; alkyl (e.g., C1-C6 alkyl); Substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxycarbonyl; alkoxycarbonyl; alkylcarbonyloxy; alkylcarbonylamino; carbamoyloxy; arylsulfonyloxy; alkylsulfonyloxy; —C(R$_7$)=N—(O)$_i$—R$_8$ wherein R$_7$ is H, alkyl, alkenyl, cycloalkyl, or aryl, i is 0 or 1, and R$_8$ is H, alkyl, alkenyl, cycloalkyl, or heterocycle; and R$_9$C(O)O— wherein R$_9$ is halogen, amino, substituted amino, heterocycle, substituted heterocycle, or R$_{10}$—O—(CH$_2$)$_m$— where m is an integer of 1-10 and R$_{10}$ is alkyl, phenyl, substituted phenyl, cycloalkyl, substituted cycloalkyl, heterocycle, or substituted heterocycle; or R$_2$ together with R$_3$ or R$_3$ together with R$_4$ form substituted or unsubstituted methylenedioxy, ethylenedioxy, or ethyleneoxy;

R$_6$ is H or OR', wherein R' is alkyl, alkenyl, cycloalkyl, haloalkyl, or hydroxyalkyl; and L is the site of attachment to X.

In yet another particular embodiment, D is irinotecan.

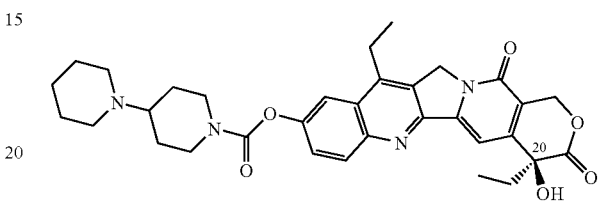

Alternatively, D is a small molecule selected from the group consisting of platins, oxymorphone analogues, steroids, quinolones, and nucleosides.

In one embodiment, D is a platin such as cis-platin, hydroxyplatin, carboplatin, or oxaliplatin.

In yet a further embodiment, D is an oxymorphone analogue such as naloxone, methylnaltrexone, oxymorphone, codeine, oxycodone, or morphine.

In yet an additional embodiment, D is a steroid such as budesonide, triamcinolone, or fluticasone.

In yet another embodiment, D is a quinolone, isoquinolone or fluoroquinolone such as ciprofloxacin, moxifloxacin, or palonosetron.

In yet an additional embodiment, D is a nucleoside or nucleotide such as gemcitabine, cladribine, or fludarabine.

The multi-armed polymer prodrugs of the invention possess many unique features, particularly in the instance where the small molecule is an anticancer compound. For example, in one embodiment, provided is a multi-armed polymer prodrug, which when evaluated in a suitable animal model for solid tumor-type cancers and administered in a therapeutically effective amount, is effective to suppress tumor growth to an extent that is at least 1.5 times that, or even twice that observed for the unmodified anticancer agent, when evaluated over a time course of 30 days. In yet another embodiment, the prodrug is effective to suppress tumor growth to the above extent or even greater when evaluated over a time course of 60 days. The small molecule employed is one known to possess anticancer properties, however, by virtue of its conjugation to a multi-armed polymer as described herein, possesses significantly improved efficacy and pharmacokinetics in comparison to the small molecule, e.g., anticancer compound, itself. Suitable solid tumor types include malignant sarcomas, carcinomas and lymphomas of the breast, ovaries, colon, kidney, bile duct, lung and brain.

In another aspect, the invention encompasses reactive multi-armed polymers suitable for preparing any of the above-described prodrug conjugates.

In another aspect, the invention encompasses a pharmaceutical composition comprising a multi-arm polymer prodrug conjugate as described above in combination with a pharmaceutically acceptable carrier.

Another aspect of the invention provides a method for treating various medical conditions in a mammalian subject.

More specifically, the invention encompasses a method of administering to a mammalian subject in need thereof a therapeutically effective amount of a multi-arm prodrug conjugate of the invention. In one embodiment, the drug moiety, D, is an anticancer agent such as a camptothecin (e.g., irinotecan), and is effective to suppress tumor growth. In a particularly preferred embodiment, a multi-armed prodrug conjugate of the invention, particularly one where D is an anticancer agent, exhibits one or more of the following characteristics: (i) suppresses tumor growth to an extent greater than that of unmodified D, (ii) demonstrates a tumor retention time that is increased over that of unmodified D, (iii) exhibits a rate of clearance that is reduced in comparison to that of unmodified D, and/or (iv) produces reduced adverse side effects in comparison to unmodified D.

According to yet another aspect, the invention provides a method of treating cancer or a viral infection by administering a multi-arm polymer conjugate as described herein.

In yet another aspect, the invention provides a method of treating a topoisomerase I inhibitor-related disease in a mammalian subject by administering a therapeutically effective amount of a multi-arm polymer prodrug to a mammalian subject in need thereof, where the small molecule is a camptothecin type molecule.

According to yet another aspect, provided herein is a method of targeting a solid tumor in a mammalian subject. The method includes the step of administering a therapeutically effective amount of a multi-arm polymer prodrug of an anticancer agent known to be effective in the treatment of solid tumors to a subject diagnosed as having one or more cancerous solid tumors. As a result of said administering, the prodrug is effective to produce an inhibition of solid tumor growth in the subject that is increased over the inhibition of solid tumor growth resulting from administration of the anticancer agent alone.

In a further aspect, a method for preparing a multi-arm polymer prodrug conjugate of the invention is provided. In the method, a small molecule, D, is provided, where the small molecule comprises a functional group, F, suitable for forming a hydrolyzable linkage, Z. The small molecule is reacted with a bifunctional spacer, Y', comprising each a first and a second functional group, F1 and F2. The functional group F2 is suitable for reaction with F, and F1 may optionally be in protected form (F1-Y'—F2). The reaction is carried out under conditions effective to form a partially modified active agent comprising a hydrolyzable linkage, Z, resulting from reaction of F and F2, which corresponds to the structure D-Z—Y'—F1. If necessary, the method includes the optional step of deprotecting F1 contained in the partially modified active agent. The method then includes the step of reacting the partially modified active agent, D-Z—Y'—F1, with a multi-armed water-soluble polymer comprising the structure, R(-Q-POLY$_1$-F3)$_q$, where R, Q, POLY$_1$, and Q are as previously defined, and F3 is a functional group that is reactive with F1. The reaction is carried out under conditions effective to promote reaction between F3 and F1 to convert Y' to Y, to thereby form a polymer prodrug having the structure, R(-Q-POLY$_1$-Y—Z-D)$_q$, where Y is a spacer fragment, and Z is a hydrolyzable linkage, which, upon hydrolysis, releases D.

In one embodiment of the method, a stoichiometric excess in an amount greater than "q" moles of the partially modified active agent, D-Z—Y'—F1, is reacted with the multi-armed water-soluble, R(-Q-POLY$_1$-F3)$_q$ to drive the reaction to completion, i.e., to covalently attach active agent to each of the reactive polymer arms.

In yet another embodiment, where the small molecule D possesses additional functional groups reactive with F2, the method further comprises the step of protecting the additional functional groups with suitable protecting groups prior to reaction with the bifunctional spacer. These protecting groups are then removed from the small molecules of the prodrug product, R(-Q-POLY$_1$-Y—Z-D)$_q$.

According to yet another aspect of the invention, provided is yet another method for preparing a multi-arm polymer prodrug of the invention. The method includes the step of providing a reactive multi-arm polymer having the structure, R(-Q-POLY$_1$-F3)$_q$, where R, Q, POLY$_1$, and q are as previously described, and F3 is a reactive functional group. The multi-arm polymer is then reacted with a bifunctional spacer, Y', comprising each a first and a second functional group, F1 and F2, wherein F1 is suitable for reaction with F3, and F1 is optionally in protected form (F1-Y'—F2). The reaction is carried out under conditions effective to form an intermediate multi-arm polymer resulting from reaction of F3 and F1, and having the structure, R(-Q-POLY$_1$-Y—F2)$_q$. The method further includes the optional step of deprotecting F2 in the intermediate multi-arm polymer, R(-Q-POLY$_1$-Y—F2)$_q$ if such is in protected form. The intermediate multi-arm polymer, R(Q-POLY$_1$-Y—F2)$_q$, is then reacted with a small molecule, D, comprising a functional group, F, suitable for forming a hydrolyzable linkage, Z, upon reaction of F with F2, under conditions effective to thereby form a prodrug having the structure, R(-Q-POLY$_1$-Y—Z-D)$_q$, where Z is a hydrolyzable linkage, which, upon hydrolysis, releases D.

Reactive functional groups such as those described above as F1, F2 and F3, are numerous and may be selected from, for example, hydroxyl, active ester (e.g., N-hydroxysuccinimidyl ester and 1-benzotriazolyl ester), active carbonate (e.g., N-hydroxysuccinimidyl carbonate, 1-benzotriazolyl carbonate, p-nitrophenyl carbonate), acid halide, acetal, aldehyde having a carbon length of 1 to 25 carbons (e.g., acetaldehyde, propionaldehyde, and butyraldehyde), aldehyde hydrate, alkenyl, acrylate, methacrylate, acrylamide, active sulfone, amine, hydrazide, thiol, alkanoic acids having a carbon length (including the carbonyl carbon) of 1 to about 25 carbon atoms (e.g., carboxylic acid, carboxymethyl, propanoic acid, and butanoic acid), isocyanate, isothiocyanate, maleimide, vinylsulfone, dithiopyridine, vinylpyridine, iodoacetamide, epoxide, glyoxal, and dione.

In one embodiment, the bifunctional spacer, Y' is an amino acid or derived from an amino acid. Representative amino acids have the structure HO—C(O)—CH(R")—NH-Gp wherein R" is H, C1-C6 alkyl, or substituted C1-C6 alkyl and Gp is an amino-protecting group. In an alternative embodiment, the bifunctional spacer, Y' possesses the structure: —C(O)—(OCH$_2$CH$_2$)$_{1-10}$—NH-Gp.

The above methods for preparing a prodrug of the invention may include the additional steps of purifying the intermediates and/or the final prodrug products, for example by size exclusion chromatography or ion exchange chromatography in instances in which the compounds to be purified contain one or more ionizable groups, such as carboxyl or amino.

These and other objects and features of the invention will become more fully apparent when read in conjunction with the following detailed description.

DETAILED DESCRIPTION

Figure 1:
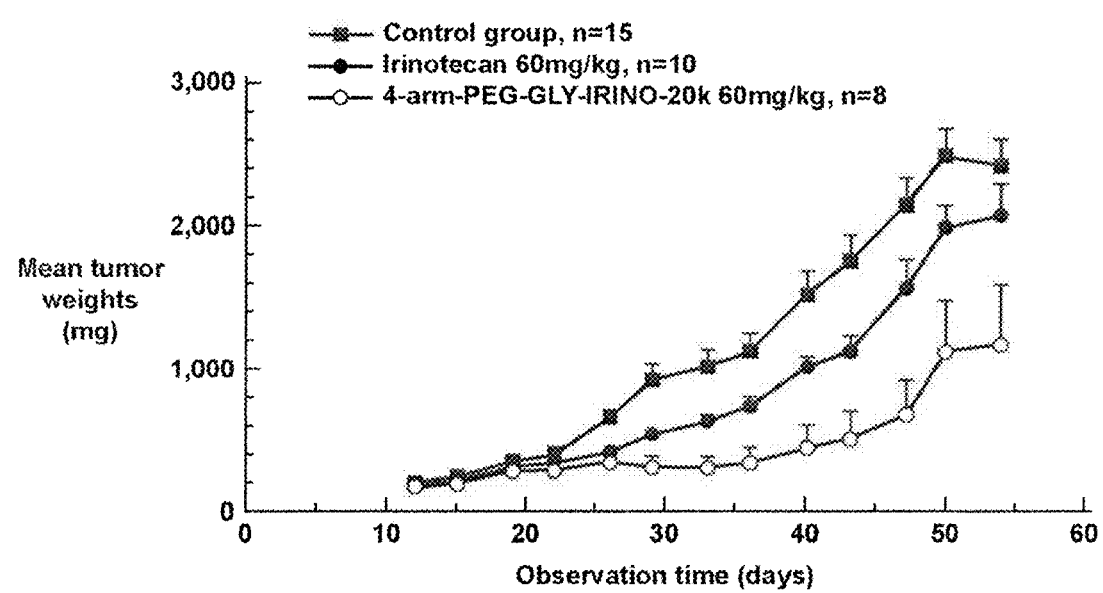
FIG. 1 is a graph illustrating the effect of an exemplary multi-arm PEG-irinotecan conjugate on the growth of HT29 human colon tumors implanted in athymic nude mice in comparison to an untreated control group and a group treated with irinotecan as described in detail in Example 2.
Figure 2:
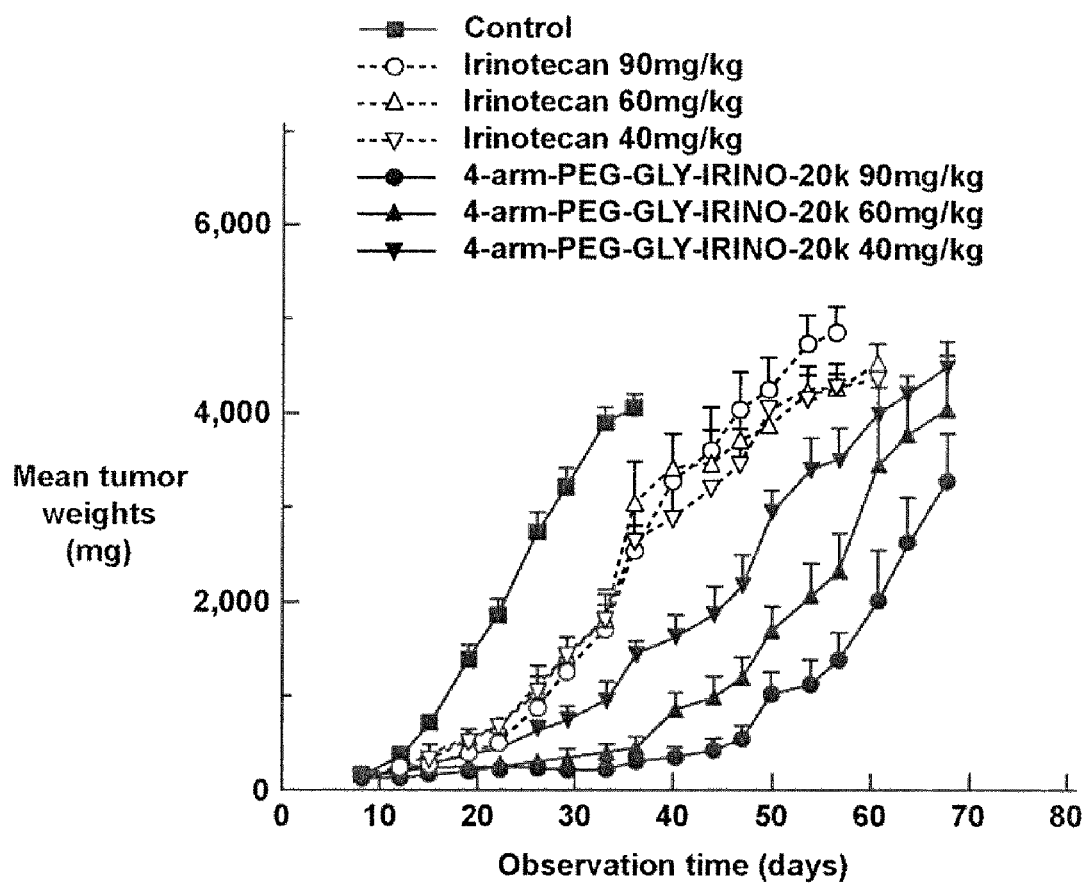
FIG. 2 is a graph illustrating the effects of a variety of doses (90 mg/kg; 60 mg/kg; and 40 mg/kg) of an exemplary 20 kilodalton (20K) multi-arm PEG irinotecan conjugate on the growth of NCI-H460 human lung tumors implanted in athymic nude mice in comparison to a control group and a group treated with irinotecan as described in Example 6.
Figure 3:
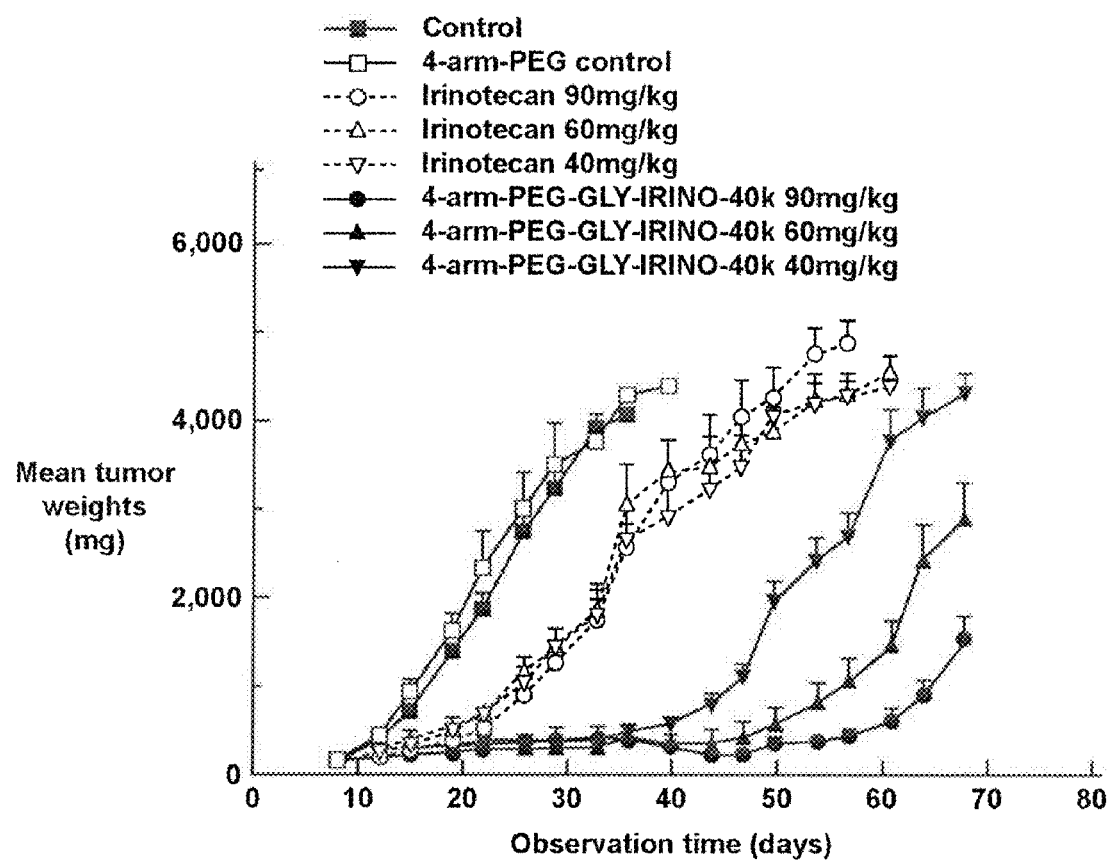
FIG. 3 is a graph illustrating the effects of a variety of doses (90 mg/kg; 60 mg/kg; and 40 mg/kg) of an exemplary 40 kilodalton (40K) multi-arm PEG irinotecan conjugate on the growth of NCI-H460 human lung tumors implanted in athymic nude mice in comparison to a control group and a group treated with irinotecan as described in Example 6.
Figure 4:
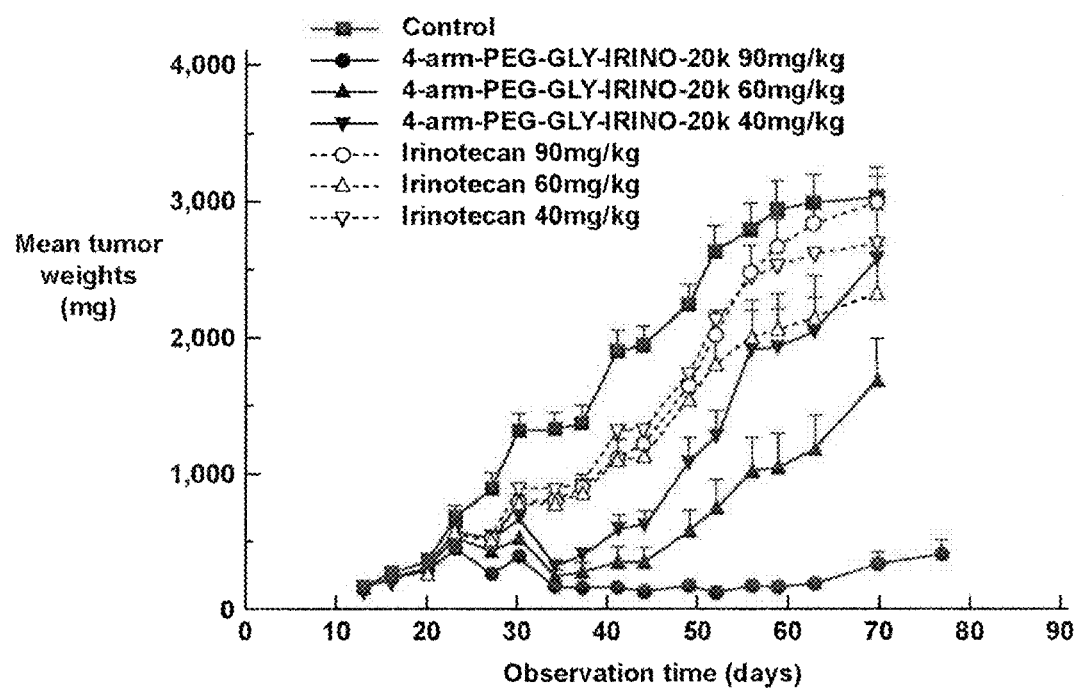
FIG. 4 is a graph illustrating the effects of a variety of doses (90 mg/kg; 60 mg/kg; and 40 mg/kg) of an exemplary 20 kilodalton (20K) multi-arm PEG-irinotecan conjugate on the growth of HT29 human colon tumors implanted in athymic nude mice in comparison to an untreated control group and a group treated with irinotecan as described in detail in Example 6.
Figure 5:
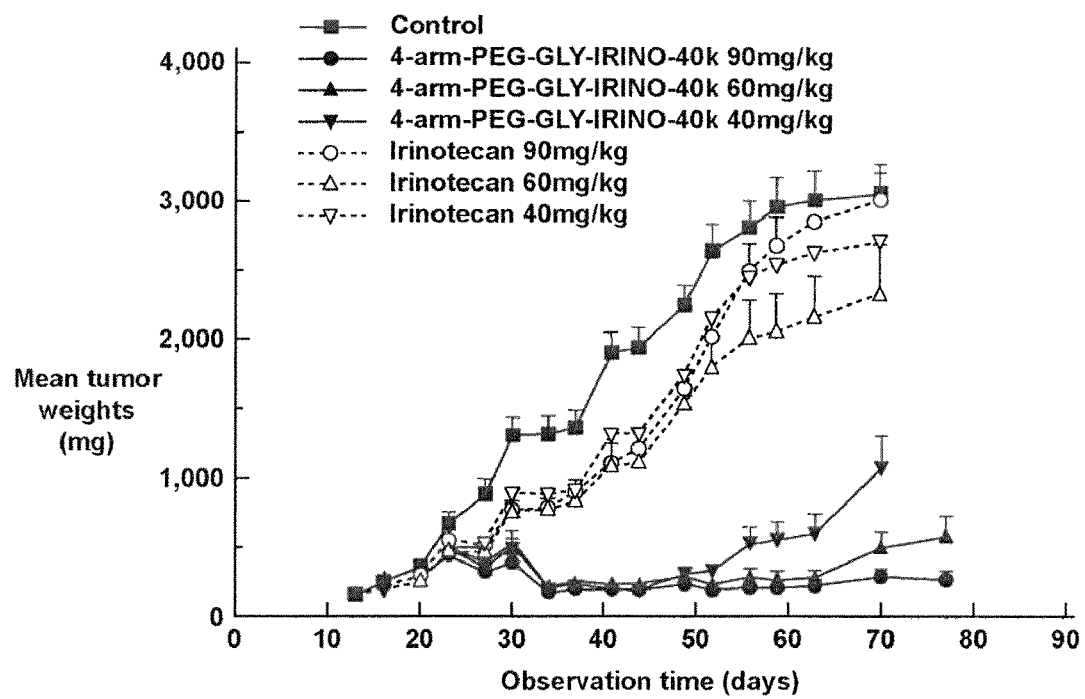
FIG. 5 is a graph illustrating the effects of a variety of doses (90 mg/kg; 60 mg/kg; and 40 mg/kg) of an exemplary 40 kilodalton (40K) multi-arm PEG-irinotecan conjugate on the growth of HT29 human colon tumors implanted in athymic nude mice in comparison to an untreated control group and a group treated with irinotecan as described in detail in Example 6.
Figure 6:
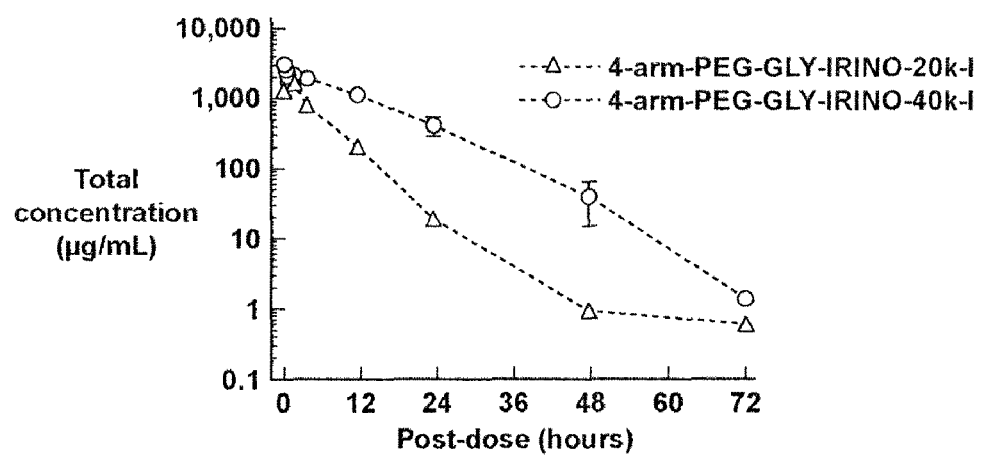
FIG. 6 is a graph illustrating the concentration in venous plasma over time of (i) an exemplary 20 kilodalton (20K) multi-arm PEG irinotecan conjugate, and (ii) a 40 kilodalton multi-arm PEG irinotecan conjugate, following IV administration as a single dose in athymic nude mice implanted with either HT29 human colon tumors or NCI-H460 human lung tumors as described in Example 7.
Figure 7:
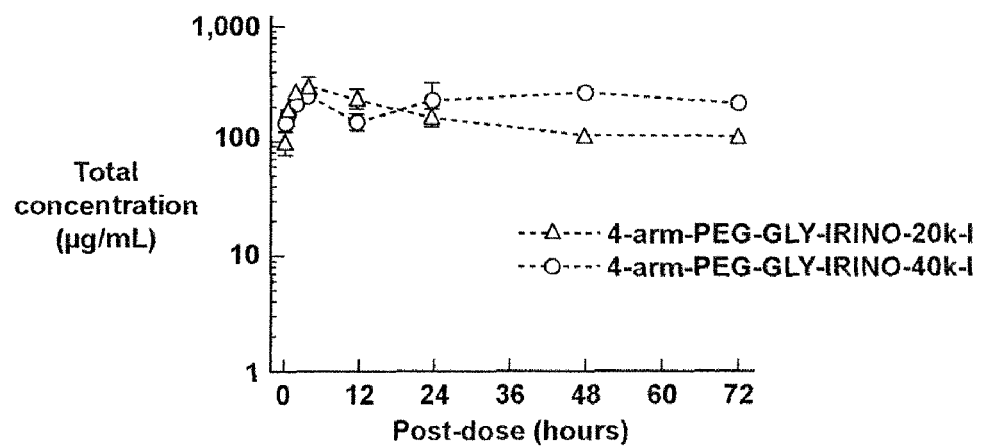
FIG. 7 is a graph illustrating the concentration in tumor tissue over time of (i) an exemplary 20 kilodalton (20K) multi-arm PEG irinotecan conjugate, and (ii) a 40 kilodalton multi-arm PEG irinotecan conjugate, following IV administration as a single dose in athymic nude mice implanted with either HT29 human colon tumors or NCI-H460 human lung tumors as described in Example 7.
Figure 8:
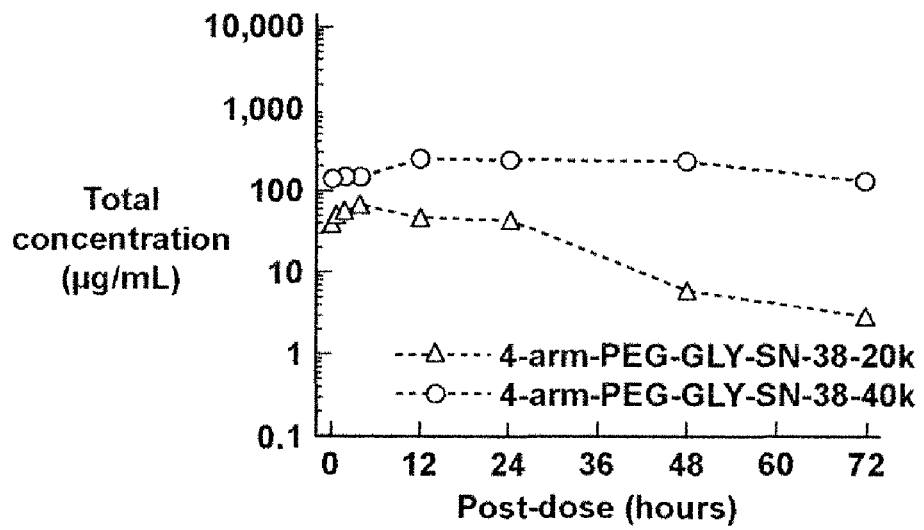
FIG. 8 is a graph illustrating the concentration of PEG-SN-38 in plasma over time following IV administration of (i) an exemplary 20 kilodalton (20K) multi-arm PEG irinotecan conjugate, or (ii) a 40 kilodalton multi-arm PEG irinotecan conjugate, as a single dose in athymic nude mice implanted with either HT29 human colon tumors or NCI-H460 human lung tumors as described in Example 7.
Figure 9:
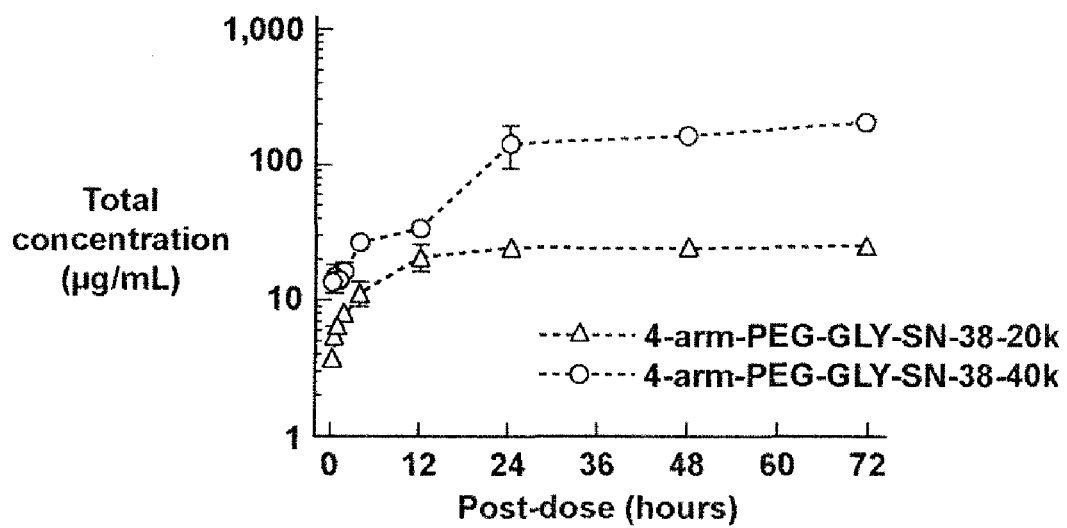
FIG. 9 is a graph illustrating the concentration of PEG SN-38 in tumor tissue over time following IV administration of (i) an exemplary 20 kilodalton (20K) multi-arm PEG irinotecan conjugate, or (ii) a 40 kilodalton multi-arm PEG irinotecan conjugate, as a single dose in athymic nude mice implanted with either HT29 human colon tumors or NCI-H460 human lung tumors as described in Example 7.
Figure 10:
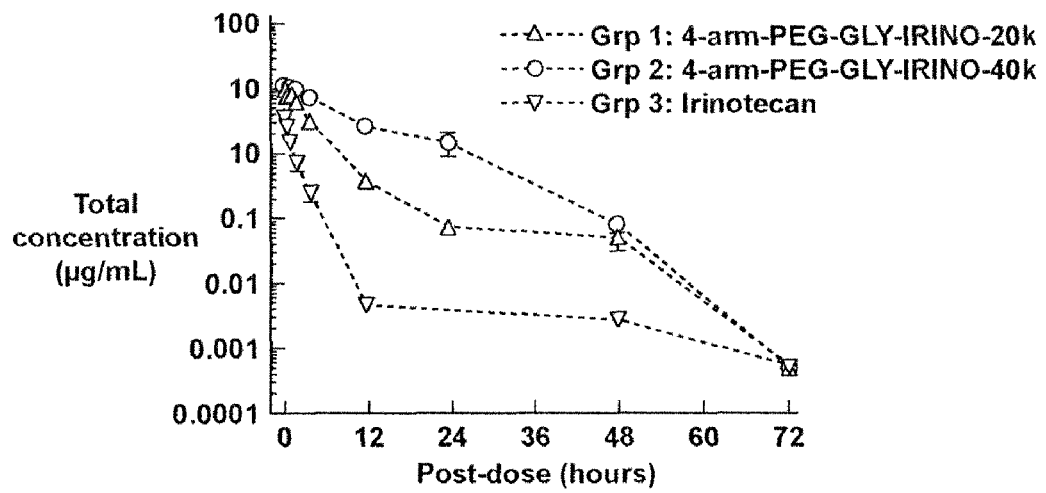
FIG. 10 is a graph illustrating the concentration of irinotecan in venous plasma over time following IV administration of (i) an exemplary 20 kilodalton (20K) multi-arm PEG irinotecan conjugate, or (ii) a 40 kilodalton multi-arm PEG irinotecan conjugate, or (iii) irinotecan itself as a single dose in athymic nude mice implanted with either HT29 human colon tumors or NCI-H460 human lung tumors as described in Example 7.
Figure 11:
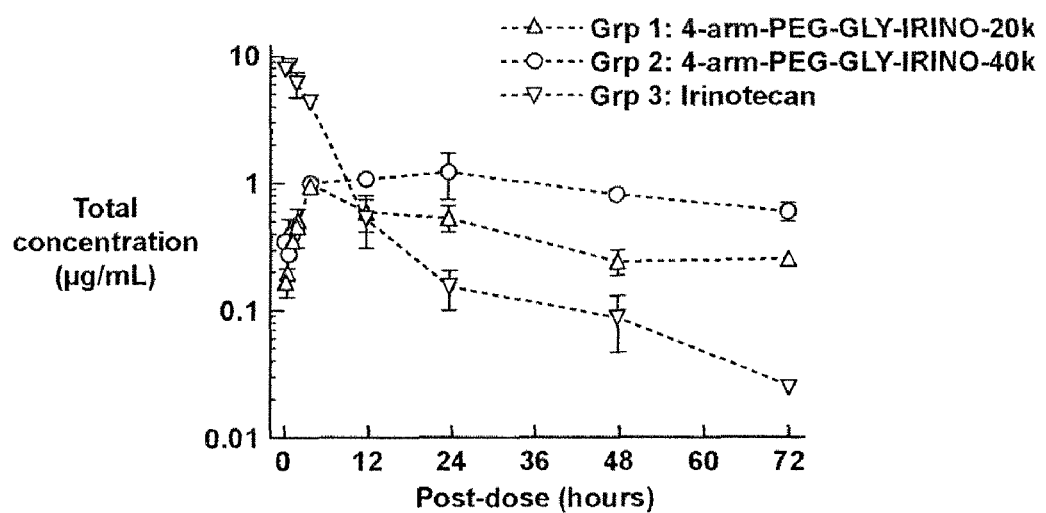
FIG. 11 is a graph illustrating the concentration of irinotecan in tumor tissue over time following IV administration of (i) an exemplary 20 kilodalton (20K) multi-arm PEG irinotecan conjugate, or (ii) a 40 kilodalton multi-arm PEG irinotecan conjugate, or (iii) irinotecan itself, as a single dose in athymic nude mice implanted with either HT29 human colon tumors or NCI-H460 human lung tumors as described in Example 7.
Figure 12:
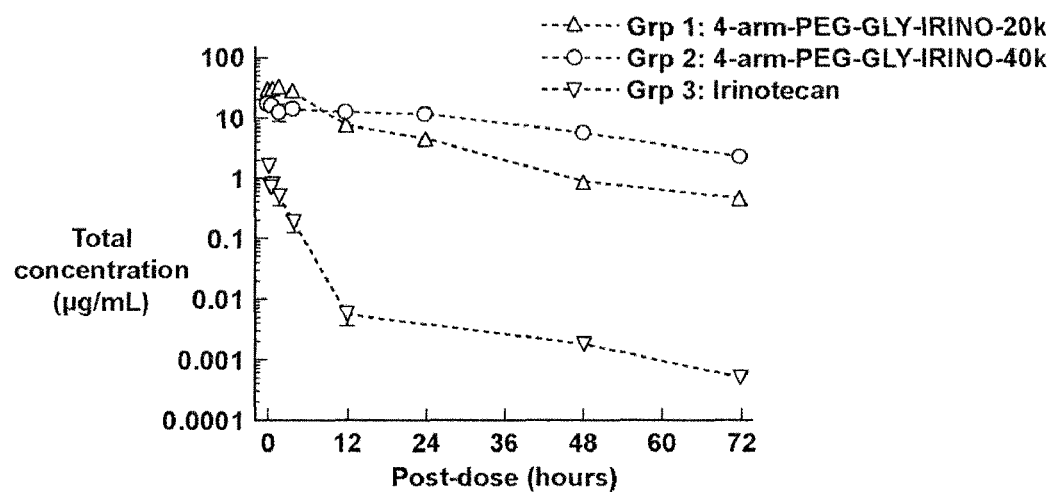
FIG. 12 is a graph illustrating the concentration of SN-38 in plasma over time following IV administration of (i) an exemplary 20 kilodalton (20K) multi-arm PEG irinotecan conjugate, or (ii) a 40 kilodalton multi-arm PEG irinotecan conjugate, or (iii) irinotecan itself, as a single dose in athymic nude mice implanted with either HT29 human colon tumors or NCI-H460 human lung tumors as described in Example 7.
Figure 13:
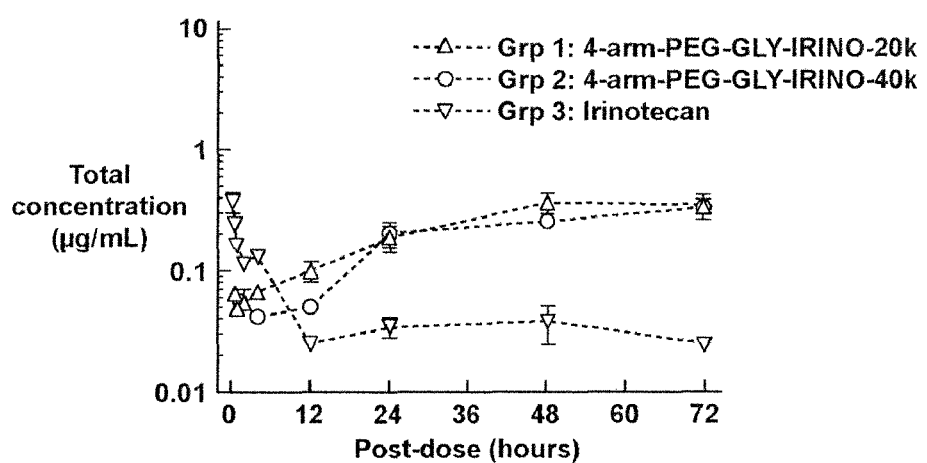
FIG. 13 is a graph illustrating the concentration of SN-38 in tumor tissue over time following IV administration of (i) an exemplary 20 kilodalton (20K) multi-arm PEG irinotecan conjugate, or (ii) a 40 kilodalton multi-arm PEG irinotecan conjugate, or (iii) irinotecan itself, as a single dose in athymic nude mice implanted with either HT29 human colon tumors or NCI-H460 human lung tumors as described in Example 7.

The present invention now will be described more fully hereinafter. This invention may, however, be embodied in many different forms and should not be construed as limited to the embodiments set forth herein; rather, these embodiments are provided so that this disclosure will be thorough and complete, and will fully convey the scope of the invention to those skilled in the art.

Definitions

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

A "functional group" is a group that may be used, under normal conditions of organic synthesis, to form a covalent linkage between the structure to which it is attached and another structure, which typically bears a further functional group. The functional group generally includes multiple bond(s) and/or heteroatom(s). Preferred functional groups for use in the polymers of the invention are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive", with reference to a functional group present on a molecule in a reaction mixture, indicates that the group remains largely intact under conditions effective to produce a desired reaction in the reaction mixture.

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include, for example, imidazolyl esters, and benzotriazole esters, and imide esters, such as N-hydroxysuccinimidyl (NHS) esters. An activated derivative may be formed in situ by reaction of a carboxylic acid with one of various reagents, e.g. benzotriazol-1-yloxy tripyrrolidinophosphonium hexafluorophosphate (PyBOP), preferably used in combination with 1-hydroxy benzotriazole (HOBT) or 1-hydroxy-7-azabenzotriazole (HOAT); O-(7-azabenzotriazol-1-yl)-N,N,N',N'-tetramethyluronium hexafluorophosphate (HATU); or bis(2-oxo-3-oxazolidinyl) phosphinic chloride (BOP-Cl).

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups which may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and references cited therein.

A functional group in "protected form" refers to a functional group bearing a protecting group. As used herein, the term "functional group" or any synonym thereof is meant to encompass protected forms thereof.

"PEG" or "poly(ethylene glycol)" as used herein, is meant to encompass any water-soluble poly(ethylene oxide). Typically, PEGs for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation. The variable (n) is 3 to 3000, and the terminal groups and architecture of the overall PEG may vary. When PEG further comprises a spacer as in structure I above (to be described in greater detail below), the atoms comprising the spacer (X), when covalently attached to a PEG segment, do not result in formation of (i) an oxygen-oxygen bond (—O—O—, a peroxide linkage), or (ii) a nitrogen-oxygen bond (N—O, O—N). "PEG" means a polymer that contains a majority, that is to say, greater than 50%, of subunits that are —$CH_2CH_2O$—. PEGs for use in the invention include PEGs having a variety of molecular weights, structures or geometries to be described in greater detail below.

"Water-soluble", in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. "R" may be saturated or unsaturated, and includes aryl, heteroaryl, cyclo, heterocyclo, and substituted forms of any of the foregoing. For instance, an end capped PEG will typically comprise the structure "RO—$(CH_2CH_2O)_n$—", where R is as defined above. Alternatively, the end-capping group can also advantageously comprise a detectable label. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, colorimetric (e.g., dyes), metal ions, radioactive moieties, and the like.

"Non-naturally occurring" with respect to a polymer of the invention means a polymer that in its entirety is not found in nature. A non-naturally occurring polymer of the invention may however contain one or more subunits or segments of subunits that are naturally occurring, so long as the overall polymer structure is not found in nature.

"Molecular mass" in the context of a water-soluble polymer of the invention such as PEG, refers to the nominal average molecular mass of a polymer, typically determined by size exclusion chromatography, light scattering techniques, or intrinsic velocity determination in 1,2,4-trichlorobenzene. The polymers of the invention are typically polydisperse, possessing low polydispersity values of less than about 1.20.

The term "linker" is used herein to refer to an atom or a collection of atoms used to link interconnecting moieties, such as an organic radical core and a polymer segment, $POLY_1$. A linker moiety may be hydrolytically stable or may include a physiologically hydrolyzable or enzymatically degradable linkage. A linker designated herein as Q is hydrolytically stable.

The term "spacer" is used herein to refer to a collection of atoms used to link interconnecting moieties, such as $POLY_1$ and the active agent, D. A spacer moiety may be hydrolytically stable or may include a physiologically hydrolyzable or enzymatically degradable linkage. A spacer designated herein as X comprises a hydrolyzable linkage, where the hydrolyzable linkage is attached directly to the active agent, D, such that upon hydrolysis, the active agent is released in its parent form.

A "hydrolyzable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Illustrative hydrolytically unstable linkages include carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes. Such a linkage requires the action of one or more enzymes to effect degradation.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multi-armed" in reference to the geometry or overall structure of a polymer refers to polymer having 3 or more polymer-containing "arms". Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of highly branched polymer is a dendritic polymer or dendrimer, that for the purposes of the invention, is considered to possess a structure distinct from that of a multi-armed polymer.

"Branch point" refers to a bifurcation point comprising one or more atoms at which a polymer splits or branches from a linear structure into one or more additional polymer arms. A multi-arm polymer may have one branch point or multiple branch points.

A "dendrimer" is a globular, size monodisperse polymer in which all bonds emerge radially from a central focal point or core with a regular branching pattern and with repeat units that each contribute a branch point. Dendrimers exhibit certain dendritic state properties such as core encapsulation, making them unique from other types of polymers.

"Substantially" or "essentially" means nearly totally or completely, for instance, 95% or greater of some given quantity.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

As used herein, "alkenyl" refers to a branched or unbranched hydrocarbon group of 1 to 15 atoms in length, containing at least one double bond, such as ethenyl, n-propenyl, isopropenyl, n-butenyl, isobutenyl, octenyl, decenyl, tetradecenyl, and the like.

The term "alkynyl" as used herein refers to a branched or unbranched hydrocarbon group of 2 to 15 atoms in length, containing at least one triple bond, ethynyl, n-propynyl, isopropynyl, n-butynyl, isobutynyl, octynyl, decynyl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, composition of matter or mixture which provides some pharmacologic, often beneficial, effect that can be demonstrated in-vivo or in vitro. This includes foods, food supplements, nutrients, nutriceuticals, drugs, vaccines, antibodies, vitamins, and other beneficial agents. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of a PEG-active agent conjugate present in a pharmaceutical preparation that is needed to provide a desired level of active agent and/or conjugate in the bloodstream or in a target tissue. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer having 3 or more functional groups, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, i.e., contains 3, 4, 5, 6, 7, 8, 9 or 10 functional groups. Typically, in reference to a polymer precursor used to prepare a polymer prodrug of the invention, the polymer possesses 3 or more polymer arms having at the terminus of each arm a functional group suitable for coupling to an active agent moiety via a hydrolyzable linkage.

"Difunctional" or "bifunctional" as used interchangeable herein means an entity such as a polymer having two functional groups contained therein, typically at the polymer termini. When the functional groups are the same, the entity is said to be homodifunctional or homobifunctional. When the functional groups are different, the polymer is said to be heterodifunctional or heterobifunctional A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The term "patient," refers to a living organism suffering from or prone to a condition that can be prevented or treated by administration of a polymer of the invention, typically but not necessarily in the form of a polymer-active agent conjugate, and includes both humans and animals.

"Optional" or "optionally" means that the subsequently described circumstance may or may not occur, so that the description includes instances where the circumstance occurs and instances where it does not.

A "small molecule" may be defined broadly as an organic, inorganic, or organometallic compound typically having a molecular weight of less than about 1000. Small molecules of the invention encompass oligopeptides and other biomolecules having a molecular weight of less than about 1000.

An "active agent moiety" in reference to a prodrug conjugate of the invention, refers to the portion or residue of the unmodified parent active agent up to the covalent linkage resulting from covalent attachment of the drug (or an activated or chemically modified form thereof) to a polymer of the invention. Upon hydrolysis of the hydrolyzable linkage between the active agent moiety and the multi-armed polymer, the active agent per se is released.

Multi-Arm Polymer Prodrug Conjugates—Overview

As described generally above, the polymer conjugates of the invention comprise a multi-arm water-soluble and non-peptidic polymer covalently attached to at least three active agent compounds. The conjugates of the invention are typically prodrugs, meaning that the active agent, attached to the polymer via a hydrolytically degradable linkage, is released over time following administration of the conjugate to a subject. Moreover, the conjugates of the invention are well-characterized, isolable, and purifiable compositions, in comparison to, for example, a degradable polymer-matrix having molecules of drug encapsulated therein. The conjugates of the invention exhibit higher drug loading characteristics when compared to their linear polymer-based counterparts, thus lowering the total dosage weight needed to treat a particular disease state. That is to say, the polymer scaffold of the invention is effective to covalently attach multiple active agent molecules thereto, thereby allowing a greater amount of therapeutic agent (i.e., active agent) to be administered per given weight of polymer when compared to a linear monofunctional or bifunctional polymer of about the same size but having only one or two active agent molecules attached thereto. The polymers used in the invention are hydrophilic in nature, thereby imparting hydrophilicity to the resulting conjugates, which, particularly in the case of water-insoluble active agents, facilitates their formulation into useful pharmaceutical compositions.

Typically, the total number average molecular weight of the overall multi-arm polymer portion of a polymer conjugate of the invention is about 1,000 daltons (Da) to about 100,000 Da, more preferably about 10,000 Da to about 60,000 Da, most preferably about 15,000 to about 60,000 Da. Multi-armed polymers having a number average molecular weight of about 5,000 Da, about 8,000 Da, about 10,000 Da, about 12,000 Da, about 15,000 Da, about 20,000 Da, about 25,000 Da, about 30,000 Da, about 35,000 Da, about 40,000 Da, about 45,000 Da, about 50,000 Da, and about 60,000 Da are particularly preferred. Multi-armed polymers having a molecular weight of 20,000 Da or greater, i.e., of about 20,000 Da, or 25,000 Da, or 30,000 Da, or 40,000 Da or 50,000 Da, or 60,000 Da, are particularly preferred for tumor-targeting applications. The actual molecular weight of the multi-armed polymer will depend, of course, on the number of polymer arms and the molecular weight of each polymer arm in the overall multi-armed polymer.

The linkage between the multi-armed polymer portion and the active agent is preferably hydrolytically degradable for in vivo release of the parent drug molecule over time. Representative hydrolytically degradable linkages corresponding to X in structure I include carboxylate ester, carbonate ester, phosphate ester, anhydride, acetal, ketal, acyloxyalkyl ether, imine, orthoester, and oligonucleotides. Esters such as carboxylate and carbonate esters are particularly preferred linkages. The particular linkage and linkage chemistry employed will depend upon the particular active agent, the presence of additional functional groups within the active agent, and the like, and can be readily determined by one skilled in the art based upon the guidance presented herein.

With respect to the multi-arm prodrug conjugates of the invention, it is not necessary for the polymer conjugate itself to exhibit biological activity, since the parent drug is released upon hydrolysis. However, in certain embodiments, the polymer conjugate maintains at least a measurable degree of activity. That is to say, in some instances, a multi-armed polymer conjugate possesses anywhere from about 1% to about 100% or more of the specific activity of the unmodified parent compound. That is to say, a multi-armed polymer prodrug of the invention will possess from about 1% to about 100% bioactivity relative to the unmodified parent active agent, prior to conjugation. Such activity may be determined using a suitable in-vivo or in-vitro model, depending upon the known activity of the particular parent compound. For anticancer drugs, in vivo anticancer activity is typically evaluated by comparison of growth rates of tumor implants in drug treated and control groups of athymic mice using well-established animal models (See for example, Examples 2 and 6). Anticancer activity is indicated by slower tumor growth rates in the treated group relative to the control group (J. W. Singer, et al., Ann. N.Y. Acad. Sci., 922: 136-150, 2000). In general, certain polymer conjugates of the invention will possess a specific activity of at least about 2%, 5%, 10%, 15%, 25%, 30%, 40%, 50%, 60%, 80%, 90% or more relative to that of the unmodified parent drug when measured in a suitable model.

As demonstrated in Examples 2, 6, and 7, preferred polymer prodrug conjugates of the invention exhibit enhanced properties in comparison to their unmodified parent drug counterparts. The polymer conjugates of the invention exhibit enhanced permeation and retention (EPR) in target tissues by passively accumulating in such tissues, to provide targeted delivery of the drug to desired sites in the body (See Matsumara Y, Maeda H. "A NEW CONCEPT FOR MACROMOLECULAR THERAPEUTICS IN CANCER THERAPY; MECHANISM OF TUMORITROPIC ACCUMULATION OF PROTEINS AND THE ANTITUMOUR AGENT SMANCS", *Cancer Res* 1986; 46:6387-92).

Additionally, the severity of the side effects associated with administration of the polymer conjugates of the invention is preferably comparable to, or even more preferably, is less than, the side effects associated with administration of the parent compound. In particular, preferred conjugates, particularly those comprising 3 or more molecules of an anticancer agent such as irinotecan, when administered to a patient, result in reduced leukopenia and diarrhea when compared to the unmodified parent drug molecule. The severity of side effects of anticancer agents such as camptothecin and camptothecin-like compounds can be readily assessed (See, for example, Kado, et al., Cancer Chemotherapy and Pharmacology, Aug. 6, 2003). The polymer conjugates of the invention are believed to exhibit reduced side effects as compared to the unconjugated parent drug, in part, due to the accumulation of the conjugate molecules in the target tissue and away from other sites of likely toxicity. Each of these features of the prodrugs of the invention will now be discussed in greater detail below.

Structural Features of the Polymer Prodrug

As described above, a prodrug of the invention comprises a multi-arm polymer, i.e., having three or more arms, where the conjugate comprises the following generalized structure:

$$R(Q\text{-}POLY_1\text{-}X\text{-}D)_q \qquad \text{I}$$

Each arm of the multi-armed prodrug is independent from the other. That is to say, each of the "q" arms of the prodrug may be composed of a different Q, $POLY_1$, X, D and so forth. Typical of such embodiments, a generalized structure corresponds to: $R[(-Q_1\text{-}POLY_{1A}\text{-}X_1\text{-}D_1)(Q_2\text{-}POLY_{1B}\text{-}X_2\text{-}D_2)(Q_3\text{-}POLY_{1C}\text{-}X_3\text{-}D_3)]$ and so forth for each of the arms emanating from the central organic core. Generally, however, each arm of the multi-armed prodrug is the same.

Each of the variable components of structure I will now be described in detail.

Organic Core, "R"

In structure I, R is an organic core radical possessing from about 3 to about 150 carbon atoms. Preferably, R contains from about 3 to about 50 carbon atoms, and even more preferably, R contains from about 3 to about 10 carbon atoms. That is to say, R may possess a number of carbon atoms selected from the group consisting of 3, 4, 5, 6, 7, 8, 9, and 10. The organic core may optionally contain one or more heteroatoms (e.g., O, S, or N), depending of course on the particular core molecule employed. R may be linear or cyclic, and typically, emanating therefrom are at least 3 independent polymer arms, three or more of which have at least one active agent moiety covalently attached thereto. Looking at Structure I, "q" corresponds to the number of polymer arms emanating from "R". In some instances one or more of the polymer arms may not have an active agent covalently attached thereto, but rather may have a relatively unreactive or unreacted functional group at its terminus, resulting from a synthesis that failed to go to completion. In this instance, D is absent and the individual structure of at least one of the polymer arms is in its precursor form (or is a derivative thereof), i.e., having at its terminus not an active agent, D, but rather an unreacted functional group.

The central core organic radical, R, is derived from a molecule that provides a number of polymer attachment sites approximately equal to the desired number of water soluble and non-peptidic polymer arms. Preferably, the central core molecule of the multi-arm polymer structure is the residue of a polyol, polythiol, or a polyamine bearing at least three hydroxyl, thiol, or amino groups available for polymer attachment. A "polyol" is a molecule comprising a plurality (greater than 2) of available hydroxyl groups. A "polythiol" is a molecule that possesses a plurality (greater than 2) thiol groups. A "polyamine" is a molecule comprising a plurality (greater than 2) of available amino groups. Depending on the desired number of polymer arms, the precursor polyol, polyamine or polythiol, (prior to covalent attachment of $POLY_1$) will typically contain 3 to about 25 hydroxyl, or amino groups or orthiol groups, respectively, preferably from 3 to about 10 hydroxyl, amino groups or thiol groups, (i.e., 3, 4, 5, 6, 7, 8, 9, 10), most preferably, will contain from 3 to about 8 (e.g., 3, 4, 5, 6, 7, or 8) hydroxyl, amino groups or thiol groups suitable for covalent attachment of $POLY_1$. The polyol, polyamine or polythiol may also include other protected or unprotected functional groups. Focusing on organic cores derived from polyols or polyamines, although the number of intervening atoms between each hydroxyl or amino group will vary, preferred cores are those having a length of from about 1 to about 20 intervening core atoms, such as carbon atoms, between each hydroxyl or amino group, preferably from about 1 to about 5. In referring to intervening core atoms and lengths, $-CH_2-$, for example, is considered as having a length of one intervening atom, although the methylene group itself contains three atoms total, since the Hs are substituents on the carbon, and $-CH_2CH_2-$, for instance, is considered as having a length of two carbon atoms, etc. The particular polyol or polyamine precursor depends on the desired number of polymer arms in the final conjugate. For example, a polyol or polyamine core molecule having 4 functional groups, Q, is suitable for preparing a prodrug in accordance with structure I having four polymer arms extending therefrom and covalently attached to active agent.

The precursor polyol or polyamine core will typically possess a structure $R-(OH)_p$ or $R-(NH_2)_p$ prior to functionalization with a polymer. The value of p corresponds to the value of q in structure I, since each functional group, typically $-OH$ or $-NH_2$, in the parent core organic molecule, if sterically accessible and reactive, is covalently attached to a polymer arm, $POLY_1$. Note that in structure I, the variable "Q", when taken together with R, typically represents a residue of the core organic radical as described herein. That is to say, when describing preferred organic core molecules, particularly by name, the core molecules are described in their precursor form, rather than in their radical form after removal of, for example, a proton. So, if for example, the organic core radical is derived from pentaerythritol, the precursor polyol possesses the structure $C(CH_2OH)_4$, and the organic core radical, together with Q, corresponds to $C(CH_2O-)_4$, where Q is O.

Illustrative polyols that are preferred for use as the polymer core include aliphatic polyols having from 1 to 10 carbon atoms and from 1 to 10 hydroxyl groups, including for example, ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glyceraldehyde, glucose, ribose, mannose, galactose, and related stereoisomers. Aromatic polyols may also be used, such as 1,1,1-tris(4'-hydroxyphenyl) alkanes, such as 1,1,1-tris(4-hydroxyphenyl)ethane, (1,3-adamantanediyl)diphenol, 2,6-bis(hydroxyalkyl)cresols, 2,2'alkylene-bis(6-t-butyl-4-alkylphenols), 2,2'-alkylene-bis(t-butylphenols), catechol, alkylcatechols, pyrogallol, fluoroglycinol, 1,2,4-benzenetriol, resorcinol, alkylresorcinols, dialkylresorcinols, orcinol monohydrate, olivetol, hydroquinone, alkylhydroquinones, 1,1-bi-2-naphthol, phenyl hydroquinones, dihydroxynaphthalenes, 4,4'-(9-fluorenylidene)-diphenol, anthrarobin, dithranol, bis (hydroxyphenyl)methane biphenols, dialkylstilbesterols, bis(hydroxyphenyl)alkanes, bisphenol-A and derivatives thereof, meso-hexesterol, nordihydroguaiaretic acid, calixarenes and derivatives thereof, tannic acid, and the like. Other core polyols that may be used include crown ethers, cyclodextrins, dextrins and other carbohydrates (e.g., monosaccharides, oligosaccharides, and polysaccharides, starches and amylase).

Preferred polyols include glycerol, trimethylolpropane, reducing sugars such as sorbitol or pentaerythritol, and glycerol oligomers, such as hexaglycerol. A 21-arm polymer can be synthesized using hydroxypropyl-β-cyclodextrin, which has 21 available hydroxyl groups.

Exemplary polyamines include aliphatic polyamines such as diethylene triamine, N,N',N''-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al., *Antimicrobial Agents and Chemotherapy*, January 2002, p. 55-61, Vol. 46, No. 1, which is incorporated by reference herein.

Provided below are illustrative structures corresponding to the organic radical portion of the conjugate, R, and the corresponding conjugate, assuming that each of the hydroxyls in the parent polyol has been transformed to a polymer arm. Note that the organic radicals shown below, derived from polyols, include the oxygens, which, in the context of structure I, for the arms that are polymer arms, are considered as part of Q. It is not necessary that all hydroxyls in, for example, a polyol-derived organic radical, form part of a polymer arm. In the illustrative examples below, Q is shown as O, but can equally be considered as corresponding to S, —NH—, or NH—C(O)—.

ORGANIC RADICAL*

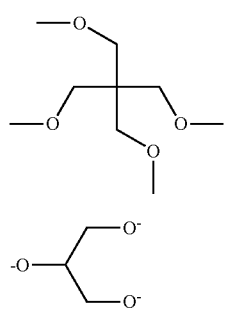

II

III

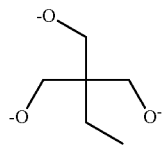

IV

V

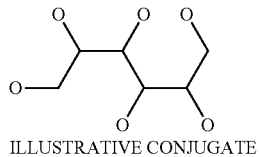

VI

ILLUSTRATIVE CONJUGATE

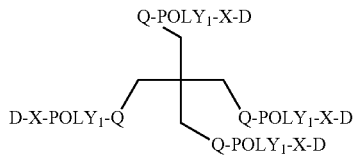

II-A

III-A

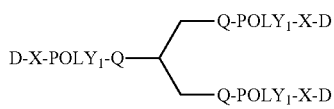

IV-A

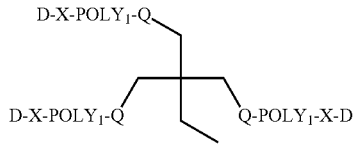

see conjugate below

V-A

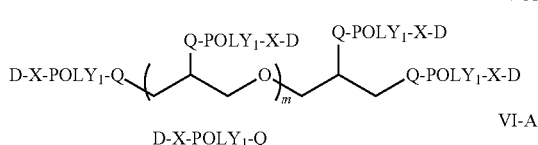

VI-A

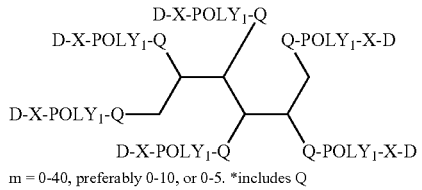

m = 0-40, preferably 0-10, or 0-5. *includes Q

Linkages, Q and X.

The linkages between the organic radical, R, and the polymer segment, $POLY_1$, or between $POLY_1$ and the active agent, D, result from the reaction of various reactive groups contained within R, $POLY_1$, and D. The particular coupling chemistry employed will depend upon the structure of the active agent, the potential presence of multiple functional groups within the active molecule, the need for protection/deprotection steps, the chemical stability of the active agent, and the like, and will be readily determined by one skilled in the art based upon the guidance herein. Illustrative linking chemistry useful for preparing the polymer conjugates of the invention can be found, for example, in Wong, S. H., (1991), "*Chemistry of Protein Conjugation and Crosslinking*", CRC Press, Boca Raton, Fla. and in Brinkley, M. (1992) "*A Brief*

Survey of Methods for Preparing Protein Conjugates with Dyes, Haptens, and Crosslinking Reagents", in *Bioconjug. Chem.*, 3, 2013. As noted above, the overall linkage between the multi-armed polymer core and each drug molecule preferably comprises a hydrolytically degradable portion, such as an ester linkage, so that the active agent is released over time from the multi-armed polymer core.

The multi-arm polymeric conjugates provided herein (as well as the corresponding reactive polymer precursor molecules, and so forth) comprise a linker segment, Q, and a spacer segment, X. Exemplary spacers or linkers can include segments such as those independently selected from the group consisting of —O—, —S—, —NH—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, and —O—C(O)—CH$_2$—CH$_2$—CH$_2$—.

In any of the above examples, a simple cycloalkylene group, e.g. 1,3- or 1,4-cyclohexylene, may replace any two, three or four carbon alkylene group. For purposes of the present disclosure, however, a series of atoms is not a spacer moiety when the series of atoms is immediately adjacent to a water-soluble polymer segment and the series of atoms is but another monomer, such that the proposed spacer moiety would represent a mere extension of the polymer chain. A spacer or linker as described herein may also comprise a combination of any two or more of the above groups, in any orientation.

Referring to structure I, Q is a linker, preferably one that is hydrolytically stable. Typically, Q contains at least one heteroatom such as O, or S, or NH, where the atom proximal to R in Q, when taken together with R, typically represents a residue of the core organic radical R. Generally, Q contains from 1 to about 10 atoms, or from 1 to about 5 atoms. Q typically contains one of the following number of atoms: 1, 2, 3, 4, 5, 6, 7, 8, 9, or 10. Illustrative Qs include O, S, or —NH—C(O)—.

Again in reference to structure I, X is a spacer that comprises a hydrolyzable linkage, where the hydrolyzable linkage is attached directly to the active agent, D. Typically, at least one atom of the hydrolyzable linkage is contained in the active agent in its unmodified form, such that upon hydrolysis of the hydrolyzable linkage comprised within X, the active agent, D, is released. Generally speaking, the spacer has an atom length of from about 4 atoms to about 50 atoms, or more preferably from about 5 atoms to about 25 atoms, or even more preferably from about 5 atoms to about 20 atoms. Typically, the spacer is of an atom length selected from the group consisting of 4, 5, 6, 7, 8, 9, 10, 11, 12, 13, 14, 15, 16, 17, 18, 19, and 20. When considering atom chain length, only atoms contributing to the overall distance are considered. For example, a spacer having the structure, —CH$_2$—C(O)—NH—CH$_2$CH$_2$O—CH$_2$CH$_2$O—C(O)—O— has a chain length of 11 atoms, since substituents are not considered to contribute significantly to the length of the spacer.

In yet another particular embodiment, X possesses the structure: Y-Z, where Y is a spacer fragment covalently attached to Z, a hydrolytically degradable linkage. In certain embodiments, Z itself may not constitute a hydrolytically degradable linkage, however, when taken together with Y, or at least a portion of Y, forms a linkage that is hydrolytically degradable.

In yet a more particular embodiment of the spacer, X, Y has the structure: —(CR$_x$R$_y$)$_a$—K—(CR$_x$R$_y$)$_b$—(CH$_2$CH$_2$O)$_c$—, wherein each R$_1$ and R$_2$, in each occurrence, is independently H or an organic radical selected from the group consisting of alkyl, substituted alkyl, alkenyl, substituted alkenyl, alkynyl, substituted alkynyl, aryl, and substituted aryl, a ranges from 0 to 12 (i.e., can be 0, 1, 2, 3, 4, 5, 6, 7, 8, 9, 10, 11, or 12), b ranges from 0 to 12 (i.e., can be 0, 1, 2, 3, 4, 5, 6, 7, 8, 9, 10, 11, or 12), K is selected from —C(O)—, —C(O)NH—, —NH—C(O)—, —O—, —S—, O—C(O)—, C(O)—O—, O—C(O)—O—, O—C(O)—NH—, NH—C(O)—O—, c ranges from 0 to 25, and Z is selected from C(O)—O—, O—C(O)—O—, —O—C(O)—NH—, and NH—C(O)—O—. The particular structure of K and of Z will depend upon the values of each of a, b, and c, such that none of the following linkages result in the overall structure of spacer X: —O—O—, NH—O—, NH—NH—.

Preferably, Y comprises (—CH$_2$)$_a$—C(O)NH—(CH$_2$)$_{0,1}$—(CH$_2$CH$_2$O)$_{0-10}$.

In yet another embodiment of the spacer, X, Y has the structure: —(CR$_x$R$_y$)$_a$—K—(CR$_x$R$_y$)$_b$—(CH$_2$CH$_2$NH)$_c$—, where the variables have the values previously described. In certain instances, the presence of the short ethylene oxide or ethyl amino fragments in spacer, X, can be useful in achieving good yields during preparation of the prodrug conjugate, since the presence of the linker can help to circumvent problems associated with steric hindrance, due to the multi-armed reactive polymer, the structure of the active agent, or a combination of both. Preferably, c is selected from the group consisting of 0, 1, 2, 3, 4, 5, 6, 7, 8, 9, and 10.

Preferably, R$_x$ and R$_y$ in each occurrence are independently H or lower alkyl. In one embodiment, R$_x$ and R$_y$ are in each occurrence H. In yet another embodiment, "a" ranges from 0 to 5, i.e., is selected from 0, 1, 2, 3, 4, or 5. In yet another embodiment, b ranges from 0 to 5, i.e., is selected from 0, 1, 2, 3, 4, or 5. In yet another embodiment, c ranges from 0 to 10. In yet another embodiment, K is —C(O)—NH. Any of the embodiments described herein is meant to apply not only to generalized structure I, but also extend to particular combinations of embodiments.

In yet another embodiment, $R_x$ and $R_y$ in each occurrence are H, a is 1, K is —C(O)—NH, and b is 0 or 1.

Particular examples of X include $CH_2$—C(O)—NH—$CH_2$—C(O)O— (here, Y corresponds to —$CH_2$—C(O)—NH—$CH_2$— and Z corresponds to —C(O)—O—), and —$CH_2$—C(O)—NH—$(CH_2CH_2O)_2$—C(O)—O— (here, Y corresponds to —$CH_2$—C(O)—NH—$(CH_2CH_2O)_2$— and Z corresponds to —C(O)—O—).

The Polymer, $POLY_1$

In structure I, $POLY_1$ represents a water-soluble and non-peptidic polymer. $POLY_1$ in each polymer arm of structure I is independently selected, although preferably, each polymer arm will comprise the same polymer. Preferably, each of the arms (i.e., each "(-Q-$POLY_1$-X-D) of structure I is identical. Any of a variety of polymers that are non-peptidic and water-soluble can be used to form a conjugate in accordance with the present invention. Examples of suitable polymers include, but are not limited to, poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), poly-phosphazene, polyoxazoline, poly(N-acryloylmorpholine), such as described in U.S. Pat. No. 5,629,384, which is incorporated by reference herein in its entirety, and copolymers, terpolymers, and mixtures of any one or more of the above.

Preferably, $POLY_1$ is a polyethylene glycol or PEG. $POLY_1$ can be in any of a number of geometries or forms, including linear chains, branched, forked, etc., although preferably $POLY_1$ is linear (i.e., in each arm of the overall multi-arm structure) or forked. A preferred structure for a multi-armed polymer prodrug having a "forked" polymer configuration is as follows:

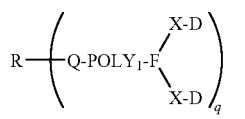

XII

F represents a forking group, and the remaining variables are as previously described. Preferably, the fork point in the forking group, F, comprises or is (—CH), though it may also be a nitrogen atom (N). In this way, each polymer arm is forked to possess two active agent moieties releasably covalently attached thereto, rather than one.

Illustrative forked polymers useful for preparing a multi-armed polymer of the type shown in FIG. XII are described in U.S. Pat. No. 6,362,254.

When $POLY_1$ is PEG, its structure typically comprises —$(CH_2CH_2O)_n$—, where n ranges from about 5 to about 400, preferably from about 10 to about 350, or from about 20 to about 300.

In the multi-arm embodiments described here, each polymer arm, $POLY_1$, typically has a molecular weight corresponding to one of the following: 200, 250, 300, 400, 500, 600, 700, 800, 900, 1000, 1500, 2000, 3000, 4000, 5000, 6000, 7000, 7500, 8000, 9000, 10000, 12,000, 15000, 17,500, 18,000, 19,000, 20,000 daltons or greater. Overall molecular weights for the multi-armed polymer configurations described herein (that is to say, the molecular weight of the multi-armed polymer as a whole) generally correspond to one of the following: 800, 1000, 1200, 1600, 2000, 2400, 2800, 3200, 3600, 4000, 6000, 8000, 12,000, 16,000, 20,000, 24,000, 28,000, 30,000, 32,000, 36,000, 40,000, 48,000, 60,000 or greater. Typically, the overall molecular weight for a multi-armed polymer of the invention ranges from about 800 to about 60,000 daltons.

Active Agent, D.

Returning now to structure I, D is an active agent moiety, and q (the number of independent polymer arms) ranges from about 3 to about 50. Preferably, q ranges from about 3 to about 25. More preferably, q is from 3 to about 10, and possesses a value of 3, 4, 5, 6, 7, 8, 9, or 10. The active agent moiety, D contains at least one functional group suitable for covalent attachment to the multi-armed polymer described herein to form a hydrolyzable linkage, such that upon hydrolysis, the active agent is released in its unmodified form.

In accordance with one embodiment of the invention, a prodrug conjugate is characterized as a polymer having from about 3 to about 25 active agent molecules covalently attached thereto. More particularly, the conjugate is characterized as a water soluble polymer having 3, 4, 5, 6, 7, 8, 9, 10, 11, 12, 13, 14, 15, 16, 17, 18, 19, 20, 21, 22, 23, 24, or 25 active agent molecules covalently attached thereto. In a further embodiment, the conjugate of the invention has from about 3 to about 8 active agent molecules covalently attached to the water-soluble polymer. Typically, although not necessarily, the number of polymer arms will correspond to the number of active agents covalently attached to the water soluble polymer.

In yet another embodiment, rather than having multiple polymer arms emanating from a central organic radical core, a conjugate of the invention is characterized as a water-soluble polymer having pendant active agent moieties covalently attached thereto, each preferably covalently attached by a degradable linkage. In such an embodiment, the structure of the polymer prodrug conjugate is described generally as $POLY_1(X-D)_q$, where and $POLY_1$, X, D, and q are as set forth above, and the polymer, typically a linear polymer, possesses "q" active agent moieties attached thereto, typically at discrete lengths along the polymer chain, via the spacer X which contains a hydrolyzable linkage.

In a specific embodiment, the active agent moiety is a small molecule possessing a molecular weight of less than about 1000. In yet additional embodiments, the small molecule drug possesses a molecular weight of less than about 800, or even less than about 750. In yet another embodiment, the small molecule drug possesses a molecular weight of less than about 500 or, in some instances, even less than about 300.

Preferred active agent moieties include anticancer agents. Particularly preferred are oncolytics having at least one hydroxyl group.

One preferred class of active agents are the camptothecins. In one embodiment, a camptothecin for use in the invention corresponds to the structure:

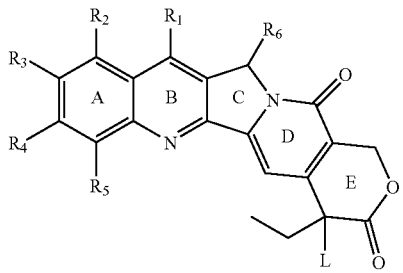

VII wherein $R_1$-$R_5$ are each independently selected from the group consisting of hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxycarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy;

$R_6$ is H or OR', wherein R' is alkyl, alkenyl, cycloalkyl, haloalkyl, or hydroxyalkyl; and L is the site of attachment to X.

In one particular embodiment, D is irinotecan, where the H on the 20-position hydroxyl is absent in the final multi-armed prodrug conjugate.

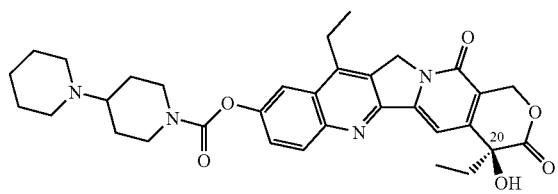

Active agents for use in the invention include hypnotics and sedatives, psychic energizers, tranquilizers, respiratory drugs, anticonvulsants, muscle relaxants, antiparkinson agents (dopamine antagonists), analgesics, anti-inflammatories, antianxiety drugs (anxiolytics), appetite suppressants, antimigraine agents, muscle contractants, anti-infectives (antibiotics, antivirals, antifungals, vaccines) antiarthritics, antimalarials, antiemetics, anepileptics, bronchodilators, cytokines, growth factors, anti-cancer agents, antithrombotic agents, antihypertensives, cardiovascular drugs, antiarrhythmics, antioxicants, anti-asthma agents, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents.

More particularly, the active agent may fall into one of a number of structural classes, including but not limited to small molecules, oligopeptides, polypeptides or protein mimetics, fragments, or analogues, steroids, nucleotides, oligonucleotides, electrolytes, and the like. Preferably, an active agent for use in the invention possesses a free hydroxyl, carboxyl, thio, amino group, or the like (i.e., "handle") suitable for covalent attachment to the polymer. Preferably, an active agent possesses at least one functional group suitable for forming a hydrolyzable linkage when reacted with a multi-armed polymer precursor suitable for forming a prodrug conjugate of the invention.

Alternatively, the drug is modified by introduction of a suitable "handle", preferably by conversion of one of its existing functional groups to a functional group suitable for formation of a hydrolyzable covalent linkage between the multi-armed polymer and the drug. Ideally, such a modification should not adversely impact the therapeutic effect or activity of the active agent to a significant degree. That is to say, any modification of an active agent to facilitate its attachment to a multi-armed polymer of the invention should result in no greater than about a 30% reduction of its bioactivity relative to the known parent active agent prior to modification. More preferably, any modification of an active agent to facilitate its attachment to a multi-armed polymer of the invention preferably results in a reduction of its activity relative to the known parent active agent prior to modification of no greater than about 25%, 20%, 15%, 10% or 5%.

Specific examples of active agents include proteins, small molecule mimetics thereof, and active fragments (including variants) of the following: aspariginase, amdoxovir (DAPD), antide, becaplermin, calcitonins, cyanovirin, denileukin diftitox, erythropoietin (EPO), EPO agonists (e.g., peptides from about 10-40 amino acids in length and comprising a particular core sequence as described in WO 96/40749), dornase alpha, erythropoiesis stimulating protein (NESP), coagulation factors such as Factor V, Factor VII, Factor VIIa, Factor VIII, Factor IX, Factor X, Factor XII, Factor XIII, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones human growth hormone (hGH), growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau, consensus interferon; interleukins and interleukin receptors such as interleukin-1 receptor, interleukin-2, interleukin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues (e.g., mono-acylated insulin as described in U.S. Pat. No. 5,922,675), amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1, endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-I antitrypsin, phosphodiesterase (PDE) compounds, VLA-4 (very late antigen-4), VLA-4 inhibitors, bisphosphonates, respiratory syncytial virus antibody, cystic fibrosis transmembrane regulator (CFTR) gene, deoxyribonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin).

Additional agents suitable include but are not limited to amifostine, amiodarone, aminocaproic acid, aminohippurate sodium, aminoglutethimide, aminolevulinic acid, aminosalicylic acid, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cilastatin sodium, cisplatin, cladribine, clodronate, cyclophosphamide, cyproterone, cytarabine, camptothecins, 13-cis retinoic acid, all trans retinoic acid; dacarbazine, dactinomycin, daunorubicin, deferoxamine, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lisinopril, lovothyroxine sodium, lomustine, mechlorethamine, medroxyprogesterone, megestrol, melphalan, mercaptopurine, metaraminol bitartrate, methotrexate, metoclopramide, mexiletine, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine, vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicillinase-sensitive agents like penicillin G, penicillin V; penicillinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefinetazole, ceftazidime, loracarbef, and moxalactam, monobactams like aztreonam; and carbapenems such as imipenem, meropenem, pentamidine isethiouate, albuterol sulfate, lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38, and tyrphostines.

The above exemplary drugs are meant to encompass, where applicable, analogues, agonists, antagonists, inhibitors, isomers, polymorphs, and pharmaceutically acceptable salt forms thereof.

As described previously, one preferred class of active agents is the camptothecins. The term "camptothecin compound" as used herein includes the plant alkaloid 20(S)-camptothecin, as well as pharmaceutically active derivatives, analogues and metabolites thereof. Examples of camptothecin derivatives include, but are not limited to, 9-nitro-20(S)-camptothecin, 9-amino-20(S)-camptothecin, 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin (SN38), 10,11-methylenedioxy camptothecin, and 10,11-ethylenedioxy camptothecin, and 7-(4-methylpiperazinomethylene)-10,11-methylenedioxy camptothecin, 7-ethyl-10-(4-(1-piperidino)-1-piperidino)-carbonyloxy-camptothecin, 9-hydroxy-camptothecin, and 11-hydroxy-camptothecin. Particularly preferred camptothecin compounds include camptothecin, irinotecan, and topotecan.

Native and unsubstituted, the plant alkaloid camptothecin can be obtained by purification of the natural extract, or may be obtained from the Stehlin Foundation for Cancer Research (Houston, Tex.). Substituted camptothecins can be obtained using methods known in the literature or can be obtained from commercial suppliers. For example, 9-nitro-camptothecin may be obtained from SuperGen, Inc. (San Ramon, Calif.), and 9-amino-camptothecin may be obtained from Idec Pharmaceuticals (San Diego, Calif.). Camptothecin and various analogues and derivatives may also be obtained from standard fine chemical supply houses, such as Sigma Chemicals.

Preferred camptothecin compounds are illustrated below in Formula XI.

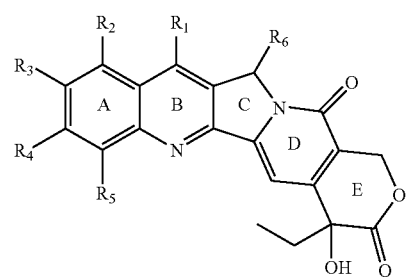

Formula XI wherein $R_1$-$R_5$ are each independently selected from the group consisting of hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxycarbonyl; alkoxycarbonyl; alkylcarbonyloxy; alkylcarbonylamino; carbamoyloxy; arylsulfonyloxy; alkylsulfonyloxy; —C(R$_7$)=N—(O)$_i$—R$_8$ wherein R$_7$ is H, alkyl, alkenyl, cycloalkyl, or aryl, i is 0 or 1, and R$_8$ is H, alkyl, alkenyl, cycloalkyl, or heterocycle; and R$_9$C(O)O— wherein R$_9$ is halogen, amino, substituted amino, heterocycle, substituted heterocycle, or R$_{10}$—O—(CH$_2$)$_m$— where m is an integer of 1-10 and R$_{10}$ is alkyl, phenyl, substituted phenyl, cycloalkyl, substituted cycloalkyl, heterocycle, or substituted heterocycle; or R$_2$ together with R$_3$ or R$_3$ together with R$_4$ form substituted or unsubstituted methylenedioxy, ethylenedioxy, or ethyleneoxy; and R$_6$ is H or OR', wherein R' is alkyl, alkenyl, cycloalkyl, haloalkyl, or hydroxyalkyl.

Exemplary substituting groups include hydroxyl, amino, substituted amino, halo, alkoxy, alkyl, cyano, nitro, hydroxycarbonyl, alkoxycarbonyl, alkylcarbonyloxy, alkylcarbonylamino, aryl (e.g., phenyl), heterocycle, and glycosyl groups.

In one embodiment of the invention, the small molecule is not taxol, or is not taxane-based.

Other preferred active agents for preparing a multi-armed polymer prodrug conjugate as described herein include platins, oxymorphone analogues, steroids, quinolones, isoquinolones, and fluoroquinolones, and nucleosides and nucleotides. Structures of illustrative compounds belonging to each of the above structural classes are provided below.

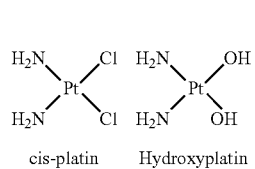
cis-platin

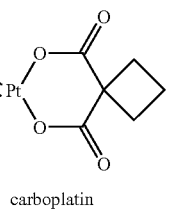
Hydroxyplatin carboplatin

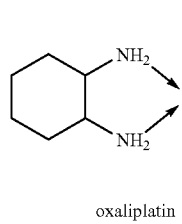
oxaliplatin

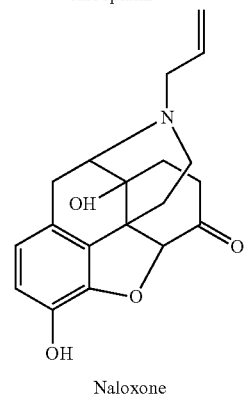
Naloxone

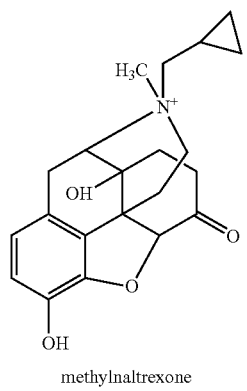
methylnaltrexone

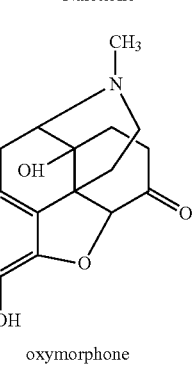
oxymorphone

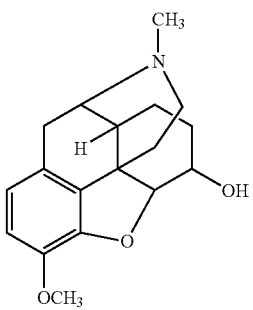
codeine

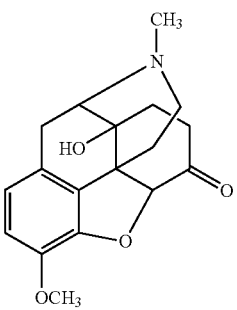
oxycodone

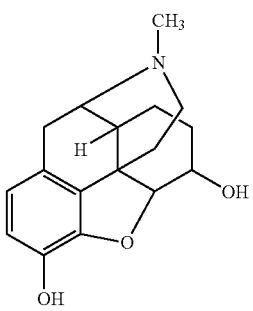
Morphine

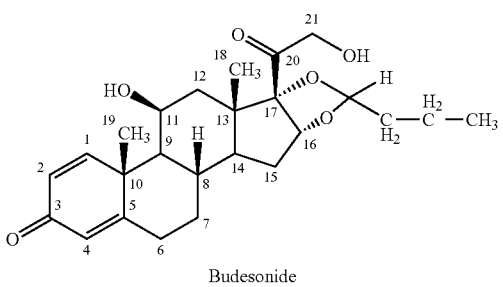
Budesonide

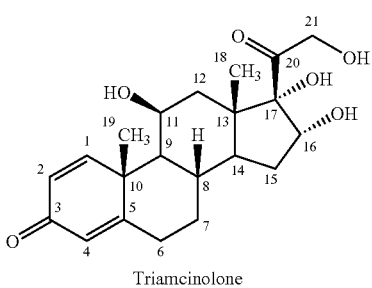
Triamcinolone

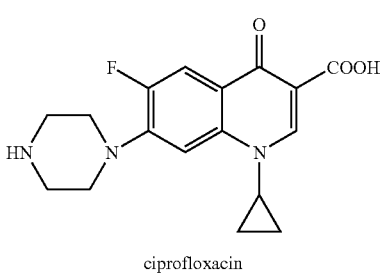
ciprofloxacin

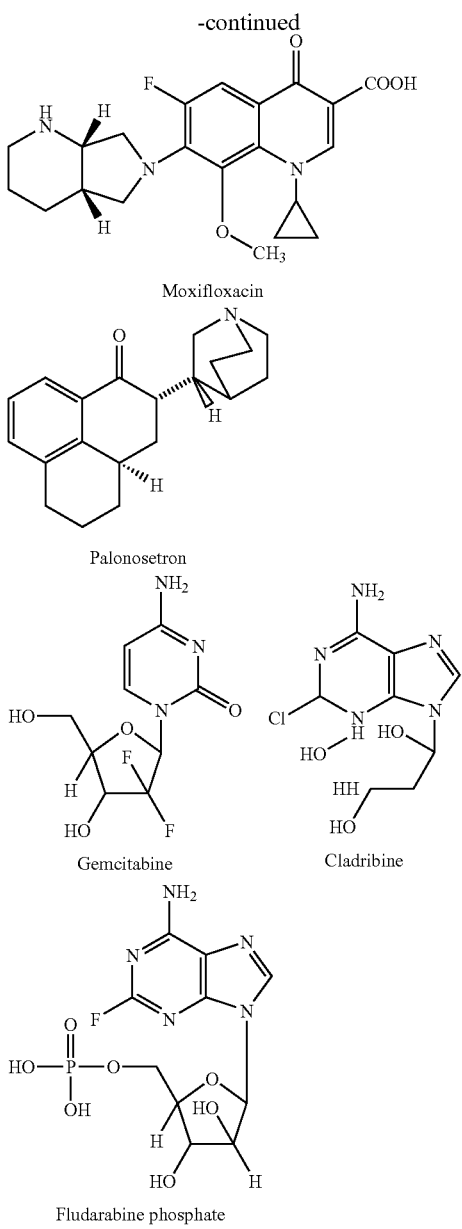

Moxifloxacin

Palonosetron

Gemcitabine

Cladribine

Fludarabine phosphate

Method of Forming a Multi-Armed Polymer Prodrug Conjugate

Multi-armed reactive polymers, such as those for preparing a prodrug of the invention can be readily prepared from commercially available starting materials in view of the guidance presented herein, coupled with what is known in the art of chemical synthesis.

Hydroxyl-terminated multi-armed PEGs having either a pentaerythritol core or a glycerol core are available from Nektar, Huntsville Ala. Such multi-armed PEGs can be used directly for coupling to active agents having, e.g., a carboxyl group in a position suitable for coupling, e.g., to provide a polymer prodrug having a hydrolyzable carboxyl ester bond. Alternatively, terminal hydroxyls present on a multi-armed polymer precursor can be oxidized to terminal carboxyl groups, e.g., for coupling to hydroxyls present on an active agent.

Alternatively, a multi-armed reactive polymer for preparing a prodrug of the invention may be synthetically prepared. For instance, any of a number of suitable polyol core materials can be purchased from a chemical supplier such as Aldrich (St. Louis, Mo.). The terminal hydroxyls of the polyol are first converted to their anionic form, using, for example, a strong base, to provide a site suitable for initiating polymerization, followed by direct polymerization of monomer subunits, e.g., ethylene oxide, onto the core. Chain building is allowed to continue until a desired length of polymer chain is reached in each of the arms, followed by terminating the reaction, e.g., by quenching.

In an alternative approach, an activated multi-armed polymer precursor to the prodrugs of the invention can be synthetically prepared by first providing a desired polyol core material, and reacting the polyol under suitable conditions with a heterobifunctional PEG mesylate of a desired length, where the non-mesylate PEG terminus is optionally protected to prevent reaction with the polyol core. The resulting multi-armed polymer precursor is then suitable for additional transformations or direct coupling to an active agent, following deprotection if necessary.

Multi-armed polymer precursors based on polyamino cores can be prepared, for example, by direct coupling to a polymer reagent activated with an acylating agent such as an NHS ester, a succinimidyl carbonate, a BTC ester or the like, to provide multi-armed polymer precursors having an amide linker, Q. Alternatively, a core molecule having multiple amino groups can be coupled with an aldehyde terminated polymer, such as a PEG, by reductive amination (using, for example, a reducing agent such as sodium cyanoborohydride) to provide a multi-armed polymer precursor having an internal amine linker, Q.

Although the polymer PEG is described as a representative polymer in the synthetic descriptions above, such approaches apply equally as well to other water-soluble polymers described herein.

The prodrugs of the invention can be formed using known chemical coupling techniques for covalent attachment of activated polymers, such as an activated PEG, to a biologically active agent (See, for example, *POLY(ETHYLENE GLYCOL) CHEMISTRY AND BIOLOGICAL APPLICATIONS*, American Chemical Society, Washington, D.C. (1997)). Selection of suitable functional groups, linkers, protecting groups, and the like to achieve a multi-arm polymer prodrug in accordance with the invention, will depend, in part, on the functional groups on the active agent and on the multi-armed polymer starting material and will be apparent to one skilled in the art, based upon the contents of the present disclosure.

A multi-armed polymer of the invention suitable for coupling to an active agent or derivatized active agent will typically have a terminal functional group such as the following: N-succinimidyl carbonate (see e.g., U.S. Pat. Nos. 5,281,698, 5,468,478), amine (see, e.g., Buckmann et al. Makromol. Chem. 182:1379 (1981), Zalipsky et al. Eur. Polym. J. 19:1177 (1983)), hydrazide (See, e.g., Andresz et al. Makromol. Chem. 179:301 (1978)), succinimidyl propionate and succinimidyl butanoate (see, e.g., Olson et al. in Poly(ethylene glycol) Chemistry & Biological Applications, pp 170-181, Harris & Zalipsky Eds., ACS, Washington, D.C., 1997; see also U.S. Pat. No. 5,672,662), succinimidyl succinate (See, e.g., Abuchowski et al. Cancer Biochem. Biophys. 7:175 (1984) and Joppich et al., Makromol. Chem. 180:1381 (1979), succinimidyl ester (see, e.g., U.S. Pat. No. 4,670, 417), benzotriazole carbonate (see, e.g., U.S. Pat. No. 5,650, 234), glycidyl ether (see, e.g., Pitha et al. Eur. J. Biochem. 94:11 (1979), Elling et al., Biotech. Appl. Biochem. 13:354 (1991), oxycarbonylimidazole (see, e.g., Beauchamp, et al., Anal. Biochem. 131:25 (1983), Tondelli et al. J. Controlled Release 1:251 (1985)), p-nitrophenyl carbonate (see, e.g., Veronese, et al., Appl. Biochem. Biotech., 11:141 (1985); and Sartore et al., Appl. Biochem. Biotech., 27:45 (1991)), aldehyde (see, e.g., Harris et al. J. Polym. Sci. Chem. Ed. 22:341 (1984), U.S. Pat. Nos. 5,824,784, 5,252,714), maleimide (see, e.g., Goodson et al. Bio/Technology 8:343 (1990), Romani et al. in Chemistry of Peptides and Proteins 2:29 (1984)), and Kogan, Synthetic Comm. 22:2417 (1992)), orthopyridyl-disulfide (see, e.g., Woghiren, et al. Bioconj. Chem. 4:314 (1993)), acrylol (see, e.g., Sawhney et al., Macromolecules, 26:581 (1993)), vinylsulfone (see, e.g., U.S. Pat. No. 5,900,461).

In turning now to one of the preferred classes of active agents, the camptothecins, since the 20-hydroxyl group of the camptothecin compound is sterically hindered, a single step conjugation reaction is difficult to accomplish in significant yields. As a result, a preferred method is to react the 20-hydroxyl group with a short linker or spacer moiety carrying a functional group suitable for reaction with a multi-arm polymer. Such an approach is applicable to many small molecules, particularly those having a site of covalent attachment that is inaccessible to an incoming reactive polymer. Preferred linkers include t-BOC-glycine or other amino acids having a protected amino group and an available carboxylic acid group (See Zalipsky et al., "Attachment of Drugs to Polyethylene Glycols", *Eur. Polym. J.*, Vol. 19, No. 12, pp. 1177-1183 (1983)). The carboxylic acid group reacts readily with the 20-hydroxyl group in the presence of a coupling agent (e.g., dicyclohexylcarbodiimide (DCC)) and a base catalyst (e.g., dimethylaminopyridine (DMAP)). Thereafter, the amino protecting group, such as t-BOC(N-tert-butoxycarbonyl), is removed by treatment with the appropriate deprotecting agent (e.g., trifluoroacetic acid (TFA) in the case of t-BOC). The free amino group is then reacted with a multi-arm or forked polymer bearing carboxylic acid groups in the presence of a coupling agent (e.g., hydroxybenzyltriazole (HOBT)) and a base (e.g., DMAP).

In a preferred embodiment, the spacer moiety is derived from and comprises an amino acid and has the structure HO—C(O)—CH(R")—NH-Gp wherein R" is H, C1-C6 alkyl, or substituted C1-C6 alkyl and Gp is a protecting group protecting the alpha-amino group of the amino acid. Typical labile protecting groups include t-BOC and FMOC (9-fluorenylmethloxycarbonyl). t-BOC is stable at room temperature and easily removed with dilute solutions of TFA and dichloromethane. FMOC is a base labile protecting group that is easily removed by concentrated solutions of amines (usually 20-55% piperidine in N-methylpyrrolidone). Preferred amino acids include alanine, glycine, isoleucine, leucine, phenylalanine, and valine.

Other spacer moieties having an available carboxylic acid group or other functional group reactive with a hydroxyl group and a protected amino group can also be used in lieu of the amino acids described above. For example, a spacer moiety having the structure HOOC-alkylene-NH-Gp may be employed, where Gp is as described above and the alkylene chain is, for example, about 1 to about 20 carbon atoms in length. Spacers comprising short —(CH$_2$CH$_2$O)$_c$— groups or (CH$_2$CH$_2$NH)$_c$ groups are also preferred, where c varies from about 0 to about 25. More particularly, c possesses a value selected from 0, 1, 2, 3, 4, 5, 6, 7, 8, 9, 10, 11, and 12.

In a particular embodiment exemplified in Example 1, conjugation is accomplished by first reacting the camptothecin compound with t-BOC-glycine, followed by deprotection of the glycine amino group and coupling of the glycine-modified camptothecin to a 4-arm PEG molecule comprising a pentaerythritol core.

In an alternative approach exemplified in Example 8, a bifunctional spacer comprising a number of —(CH$_2$CH$_2$O)— subunits is provided. One terminal functional group of the spacer is an acid chloride (—O—C(O)—Cl) suitable for reaction with an active agent hydroxyl group to form a carbonate ester (i.e., a hydrolyzable linkage), while the other terminal functional group is a protected amine. The bifunctional spacer is coupled to irinotecan, in particular to the 20-position hydroxyl thereof, in the presence of a coupling agent such as DMAP to provide a partially modified active agent. In the partially modified active agent, a hydrolyzable bond, Z, has been introduced, coupled to a spacer, Y' having a protected terminus, which upon deprotection, is suitable for reaction with an activated multi-armed polymer. The partially modified active agent is then reacted with a multi-armed polymer precursor having a reactive terminus suitable for coupling to an amine, to provide a stable amide linkage as part of the overall linkage, X.

The prodrug product may be further purified. Methods of purification and isolation include precipitation followed by filtration and drying, as well as chromatography. Suitable chromatographic methods include gel filtration chromatography and ion exchange chromatography.

Pharmaceutical Compositions

The invention provides pharmaceutical formulations or compositions, both for veterinary and for human medical use, which comprise one or more polymer prodrugs of the invention or a pharmaceutically acceptable salt thereof, with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-(β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80", and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy", 19th ed., Williams & Williams, (1995), and in the "Physician's Desk Reference", 52nd ed., Medical Economics, Montvale, N.J. (1998), and in "Handbook of Pharmaceutical Excipients", Third Ed., Ed. A. H. Kibbe, Pharmaceutical Press, 2000.

The prodrugs of the invention may be formulated in compositions including those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent or compound (i.e., the prodrug) into association with a carrier that constitutes one or more accessory ingredients. In general, the compositions are prepared by bringing the active compound into association with a liquid carrier to form a solution or a suspension, or alternatively, bring the active compound into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter. Particularly preferred are sterile, lyophilized compositions that are reconstituted in an aqueous vehicle prior to injection.

A preferred formulation is a solid formulation comprising the multi-arm polymer prodrug where the active agent, D, is irinotecan. The solid formulation comprises sorbitol and lactic acid, and is typically diluted with 5% dextrose injection or 0.9% sodium chloride injection prior to intravenous infusion.

The amount of polymer conjugate in the formulation will vary depending upon the specific opioid antagonist employed, its activity in conjugated form, the molecular weight of the conjugate, and other factors such as dosage form, target patient population, and other considerations, and will generally be readily determined by one skilled in the art. The amount of conjugate in the formulation will be that amount necessary to deliver a therapeutically effective amount of camptothecin compound to a patient in need thereof to achieve at least one of the therapeutic effects associated with the camptothecin compound, e.g., treatment of cancer. In practice, this will vary widely depending upon the particular conjugate, its activity, the severity of the condition to be treated, the patient population, the stability of the formulation, and the like. Compositions will generally contain anywhere from about 1% by weight to about 99% by weight prodrug, typically from about 2% to about 95% by weight prodrug, and more typically from about 5% to 85% by weight prodrug, and will also depend upon the relative amounts of excipients/additives contained in the composition. More specifically, the composition will typically contain at least about one of the following percentages of prodrug: 2%, 5%, 10%, 20%, 30%, 40%, 50%, 60%, or more by weight.

Compositions of the present invention suitable for oral administration may be presented as discrete units such as capsules, cachets, tablets, lozenges, and the like, each containing a predetermined amount of the active agent as a powder or granules; or a suspension in an aqueous liquor or non-aqueous liquid such as a syrup, an elixir, an emulsion, a draught, and the like.

A tablet may be made by compression or molding, optionally with one or more accessory ingredients. Compressed tablets may be prepared by compressing in a suitable machine, with the active compound being in a free-flowing form such as a powder or granules which is optionally mixed with a binder, disintegrant, lubricant, inert diluent, surface active agent or dispersing agent. Molded tablets comprised with a suitable carrier may be made by molding in a suitable machine.

A syrup may be made by adding the active compound to a concentrated aqueous solution of a sugar, for example sucrose, to which may also be added any accessory ingredient(s). Such accessory ingredients may include flavorings, suitable preservatives, an agent to retard crystallization of the sugar, and an agent to increase the solubility of any other ingredient, such as polyhydric alcohol, for example, glycerol or sorbitol.

Formulations suitable for parenteral administration conveniently comprise a sterile aqueous preparation of the prodrug conjugate, which can be formulated to be isotonic with the blood of the recipient.

Nasal spray formulations comprise purified aqueous solutions of the active agent with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye, Topical formulations comprise the active compound dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, by inhalation. These formulations comprise a solution or suspension of the desired polymer conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

Methods of Use

The multi-armed polymer prodrugs of the invention can be used to treat or prevent any condition responsive to the unmodified active agent in any animal, particularly in mammals, including humans.

The prodrugs of the invention are particularly useful as anticancer agents, i.e., have been shown to be effective in significantly reducing the growth of certain representative lung and colon cancers in in-vivo studies. In particular, the prodrugs of the invention have been shown to be nearly five times more effective at preventing the growth of human lung cancer tumors and human colon cancer tumors than the corresponding anticancer agent per se, when administered at comparable doses over illustrative time periods ranging from 30 to 80 days.

The multi-armed polymer prodrugs of the invention, in particular, those where the small molecule drug is an anticancer agent such as a camptothecin compound as described herein or other oncolytic, are useful in treating breast cancer, ovarian cancer, colon cancer, gastric cancer, malignant melanoma, small cell lung cancer, thyroid cancers, kidney cancer, cancer of the bile duct, brain cancer, lymphomas, leukemias, rhabdomyosarcoma, neuroblastoma, and the like. The prodrugs of the invention are particularly effective in targeting and accumulating in solid tumors. The prodrugs are also useful in the treatment of HIV and other viruses.

Methods of treatment comprise administering to a mammal in need thereof a therapeutically effective amount of a composition or formulation containing a polymer prodrug of the invention.

A therapeutically effective dosage amount of any specific prodrug will vary from conjugate to conjugate, patient to patient, and will depend upon factors such as the condition of the patient, the activity of the particular active agent employed, and the route of delivery.

For camptothecin-type active agents, dosages from about 0.5 to about 100 mg camptothecin/kg body weight, preferably from about 10.0 to about 60 mg/kg, are preferred. When administered conjointly with other pharmaceutically active agents, even less of the prodrug may be therapeutically effective.

Methods of treatment also include administering a therapeutically effective amount of a composition or formulation containing a multi-arm polymer prodrug of a camptothecin compound as described herein, in conjunction with a second anticancer agent. Preferably, such camptothecin type prodrugs are administered in combination with 5-fluorouracil and folinic acid, as described in U.S. Pat. No. 6,403,569. The prodrug of the invention may be administered once or several times a day, preferably once a day or less. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

HCl hydrochloric acid
MeOH methanol
CM carboxymethylene
HOBT hydroxybenzyltriazole
TFA trifluoroacetic acid
RT room temperature
SCM succinimidyl Example 1

SYNTHESIS OF PENTAERYTHRITOLYL-4-ARM-(PEG-1-METHYLENE-2OXO-VINYLAMINO ACETATE LINKED-IRINOTECAN)-20K

EXAMPLES

It is to be understood that while the invention has been described in conjunction with certain preferred specific A. Synthesis of t-Boc-Glycine-Irinotecan Reaction Scheme:

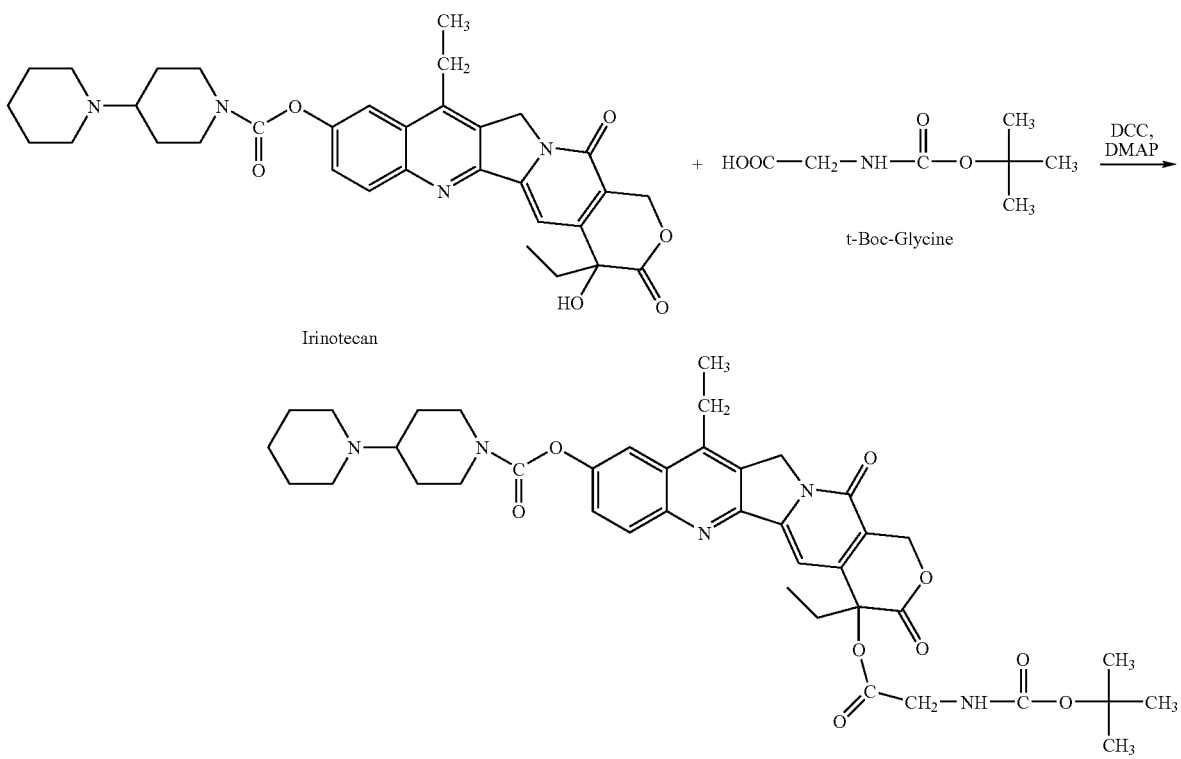

embodiments thereof, the foregoing description as well as the examples that follow are intended to illustrate and not limit the scope of the invention. Other aspects, advantages and modifications within the scope of the invention will be apparent to those skilled in the art to which the invention pertains.

All PEG reagents referred to in the appended examples are available from Nektar Therapeutics, Huntsville, Ala. All $^1$HNMR data was generated by a 300 or 400 MHz NMR spectrometer manufactured by Bruker.

Abbreviations
DCM: dichloromethane
DCC dicyclohexylcarbodiimide
DMAP dimethylaminopyridine In a flask, 0.1 g Irinotecan (0.1704 mmoles), 0.059 g t-Boc-Glycine (0.3408 mmoles), and 0.021 g DMAP (0.1704 mmoles) were dissolved in 13 mL of anhydrous dichloromethane (DCM). To the solution was added 0.070 g DCC (0.3408 mmoles) dissolved in 2 mL of anhydrous DCM. The solution was stirred overnight at room temperature. The solid was removed through a coarse frit, and the solution was washed with 10 mL of 0.1N HCL in a separatory funnel. The organic phase was further washed with 10 mL of deionized $H_2O$ in a separatory funnel and then dried with $Na_2SO_4$. The solvent was removed using rotary evaporation and the product was further dried under vacuum. $^1$H NMR (DMSO): δ 0.919 (t, $CH_2CH_3$), 1.34 (s, $C(CH_3)_3$), 3.83 (m, $CH_2$), 7.66 (d, aromatic H).

B. Deprotection of t-Boc-Glycine-Irinotecan

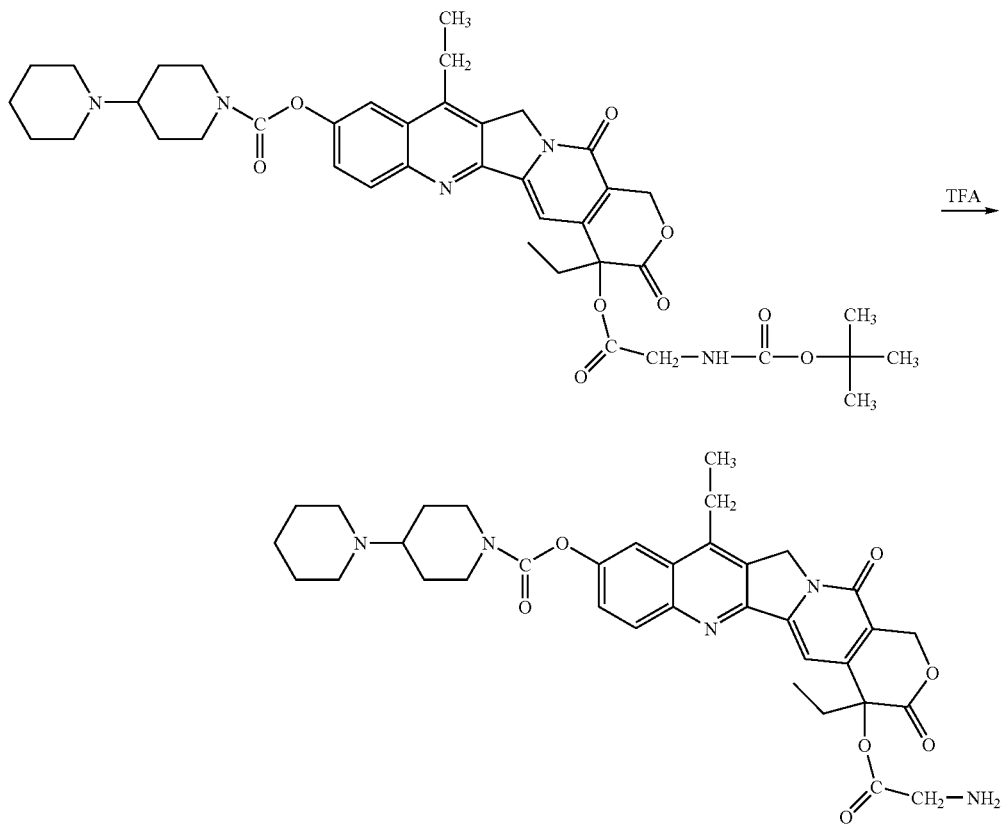

0.1 g t-Boc-Glycine-Irinotecan (0.137 mmoles) was dissolved in 7 mL of anhydrous DCM. To the solution was added 0.53 mL trifluoroacetic acid (6.85 mmoles). The solution was stirred at room temperature for 1 hour. The solvent was removed using rotary evaporation. The crude product was dissolved in 0.1 mL MeOH and then precipitated in 25 mL of ether. The suspension was stirred in an ice bath for 30 minutes. The product was collected by filtration and dried under vacuum. $^1$H NMR (DMSO): δ 0.92 (t, $CH_2CH_3$), 1.29 (t, $CH_2CH_3$), 5.55 (s, 2H), 7.25 (s, aromatic H).

C. Covalent Attachment of a Multi-Armed Activated Polymer to Glycine Irinotecan

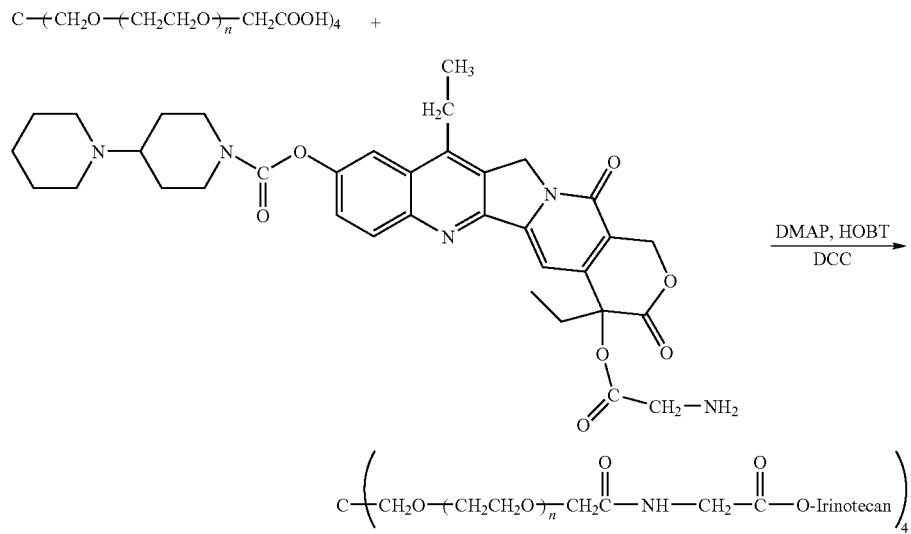

IX 0.516 g Glycine-Irinotecan (0.976 mmoles), 3.904 g 4arm-PEG(20K)-CM (0.1952 mmoles), 0.0596 g 4-(dimethylamino)pyridine (DMAP, 0.488 mmoles), and 0.0658 g 2-hydroxybenzyltriazole (HOBT, 0.488 mmoles) were dissolved in 60 mL anhydrous methylene chloride. To the resulting solution was added 0.282 g 1,3-dicyclohexylcarbodiimide (DCC, 1.3664 mmoles). The reaction mixture was stirred overnight at room temperature. The mixture was filtered through a coarse frit and the solvent was removed using rotary evaporation. The syrup was precipitated in 200 mL of cold isopropanol over an ice bath. The solid was filtered and then dried under vacuum. Yield: 4.08 g. $^1$H NMR (DMSO): δ 0.909 (t, $CH_2CH_3$), 1.28 (m, $CH_2CH_3$), 3.5 (br m, PEG), 3.92 (s, $CH_2$), 5.50 (s, 2H).

Example 2

ANTI-TUMOR ACTIVITY OF PENTAERYTHRITOLYL-4-ARM-(PEG-1-METHYLENE-2OXO-VINYLAMINO ACETATE LINKED-IRINOTECAN)-20K, "4-ARM-PEG-GLY-IRINO-20K" IN A COLON CANCER MOUSE XENOGRAFT MODEL

Human HT29 colon tumor xenografts were subcutaneously implanted in athymic nude mice. After about two weeks of adequate tumor growth (100 to 250 mg), these animals were divided into different groups of ten mice each. One group was dosed with normal saline (control), a second group was dosed with 60 mg/kg of irinotecan, and the third group was dosed with 60 mg/kg of the 4-arm PEG-GLY-Irino-20K (dose calculated per irinotecan content). Doses were administered intraveneously, with one dose administered every 4 days for a total of 3 administered doses. The mice were observed daily and the tumors were measured with calipers twice a week. FIG. 1 shows the effect of irinotecan and PEG-irinotecan treatment on HT29 colon tumors in athymic nude mice.

As can be seen from the results depicted in FIG. 1, mice treated with both irinotecan and 4-arm-PEG-GLY-Irino-20K exhibited a delay in tumor growth (anti-tumor activity) that was significantly improved when compared to the control. Moreover, the delay in tumor growth was significantly better for the 4-arm-PEG-GLY-Irino-20K group of mice when compared to the group of animals administered unconjugated irinotecan.

Example 3

SYNTHESIS OF PENTAERYTHRITOLYL-4-ARM-(PEG-1-METHYLENE-2OXO-VINYLAMINO ACETATE LINKED-IRINOTECAN)-40K, "4-ARM-PEG-GLY-IRINO-40K"

4-arm-PEG-GLY-IRINO-40K was prepared in an identical fashion to that described for the 20K compound in Example 1, with the exception that in step C, the multi-armed activated PEG reagent employed was 4 arm-PEG(40K)-CM rather than the 20K material.

Example 4

SYNTHESIS OF PENTAERYTHRITOLYL-4-ARM-(PEG-1-METHYLENE-2OXO-VINYLAMINO ACETATE LINKED-SN-38)-20K, "4-ARM-PEG-GLY-SN-38-20K"

4-arm PEG-GLY-SN-38-20K was prepared in a similar fashion to its irinotecan counterpart as described in Example 1, with the exception that the active agent employed was SN-38, an active metabolite of camptothecin, rather than irinotecan, where the phenolic-OH of SN-38 was protected with MEMCl (2-methoxyethoxymethyl chloride) during the chemical transformations, followed by deprotection with TEA to provide the desired multi-armed conjugate.

Example 5

SYNTHESIS OF PENTAERYTHRITOLYL-4-ARM-(PEG-1-METHYLENE-2OXO-VINYLAMINO ACETATE LINKED-SN-38)-40K, "4-ARM-PEG-GLY-SN-38-40K"

4-arm PEG-GLY-SN-38-40K was prepared in a similar fashion to the 20K version described above, with the exception that the multi-armed activated PEG reagent employed was 4 arm-PEG(40K)-CM rather than the 20K material.

Example 6

Additional Xenograft Studies

Additional mouse xenograft studies were conducted to further examine the efficacy of exemplary multi-armed polymer conjugates of the invention.

Athymic nude mice were implanted subcutaneously with human cancer cell lines (lung cancer cell line NCI-H460, and colon cancer cell line HT-29) and the tumors allowed to grow to approximately 150 mg in size. The animals were divided into groups of ten mice each.

Various compounds and doses were evaluated as follows: irinotecan (40, 60 and 90 mg/kg); 4-arm-PEG-GLY-IRINO-20K (40, 60, and 90 mg/kg); 4-arm-PEG-GLY-IRINO-40K ((40, 60, and 90 mg/kg); 4-arm-PEG-GLY-SN-38-20K (7.5, 15, 30 mg/kg), and PEG-GLY-SN-38-40K (7.5, 15, 30 mg/kg). Doses were administered intraveneously, with one dose administered every 4 days for a total of 3 administered doses.

Tumor volume measurements were taken over a period of 60-80 days; tumor volumes were converted to tumor weight. Body weights were also measured over the same period to provide an indication of weight loss. The results are presented graphically in FIGS. 2-5.

Example 7

PK Study—Colon Tumor Xenograft in Mice

A comparative single dose pharmacokinetic (PK) study of a multi-armed PEG-irinotecan versus unmodified irinotecan in nude mice was conducted to assess tumor distribution of parent and metabolite drug.

The study employed 108 nude mice, 36 mice per group, 4 animals per sample point. Drug was administered intravenously as a single dose. Drug form and doses were as follows: irinotecan (40 mg/kg); 4-arm-PEG-GLY-IRINO-20K (40 mg/kg equivalents); 4-arm-PEG-GLY-IRINO-40K ((40 mg/kg equivalents). Venous plasma and tumor tissue samples were taken at the following time points: 20 minutes, 40 minutes, and 1, 2, 4, 12, 24, 48, and 72 hours, and evaluated for concentrations of the following species: 4-arm-PEG-GLY-IRINO-20K, 4-arm-PEG-GLY-IRINO-40K, irinotecan and SN-38. The results are plotted in FIGS. 6 to 13.

As can be seen in FIGS. 6-13, based upon the rate of decline of the multi-armed PEGylated species in tumor tissue in comparison to plasma, the PEGylated species demonstrate a notable increase in tumor retention time when compared to unmodified parent drug.

In looking at the metabolite results, the concentrations of SN-38 derived from the PEGylated compounds appear to be increasing at the end of the 72 hour period, while in contrast, SN-38 derived from irinotecan is essentially cleared in 12 hours. In sum, the tumor exposure to SN38 following administration of either of the PEGylated compounds is approximately five times greater than for irinotecan over the same 72 hour sampling period. In sum, both multi-arm PEGylated compounds provide an increased inhibition of tumor growth (colon and lung) for both in-vivo tumor models investigated in comparison to unmodified drug. More specifically, both multi-arm PEGylated compounds demonstrated a marked suppression of tumor growth when compared to unmodified drug in mouse xenograft models, indicating the effectiveness of such compounds as anti-cancer agents. Lastly, administration of the multi-arm PEGylated irinotecan compounds described herein appears to cause less diarrhea in rats than irinotecan itself.

Example 8

SYNTHESIS OF PENTAERYTHRITOLYL-4-ARM-(PEG-2-{2-[2-1-HYDROXY-2-OXO-VINYLOXY)-ETHOXY]-ETHYLAMINO}-PROPEN-1-ONE LINKED-IRINOTECAN)-20K AND -40K

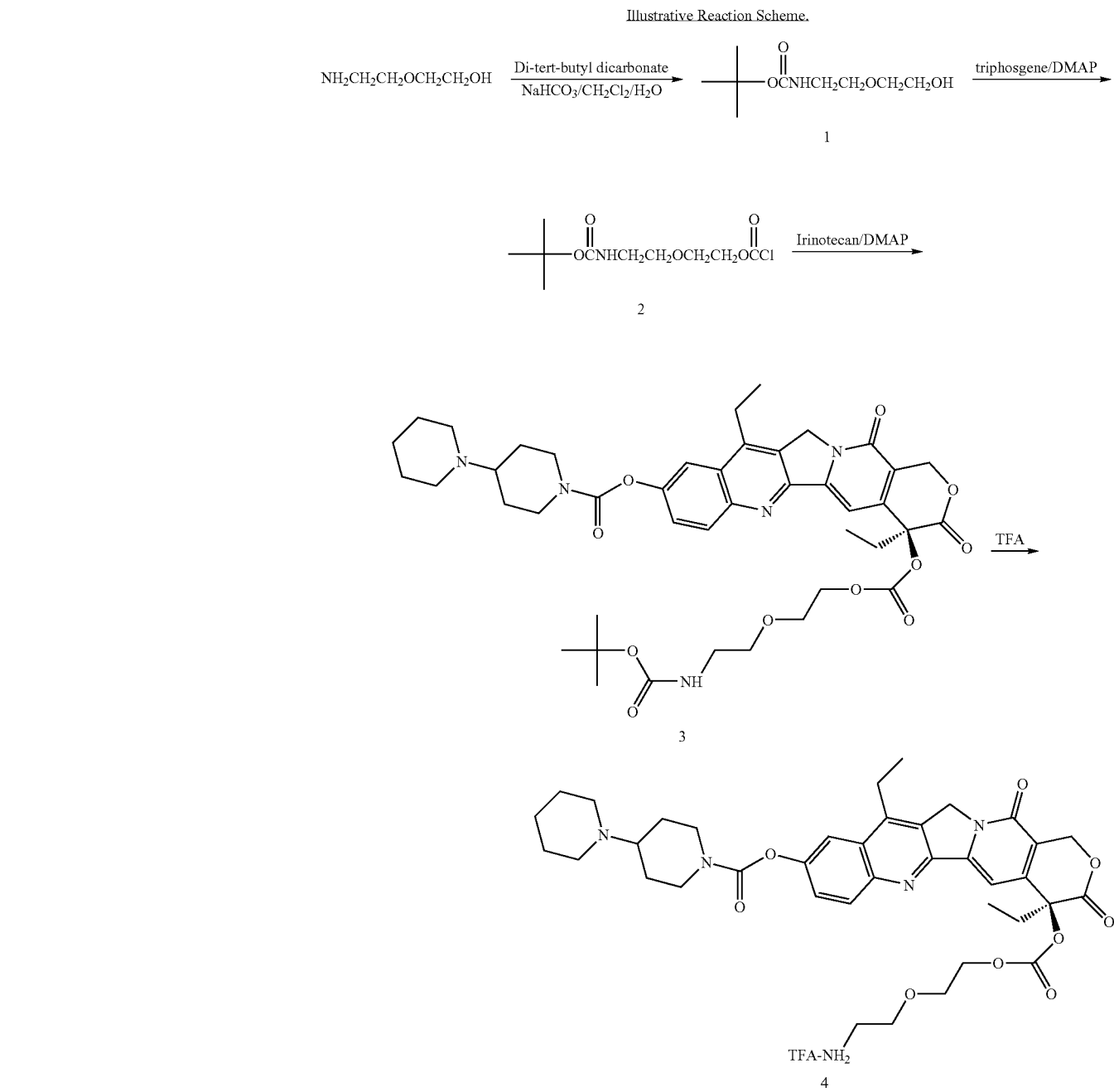

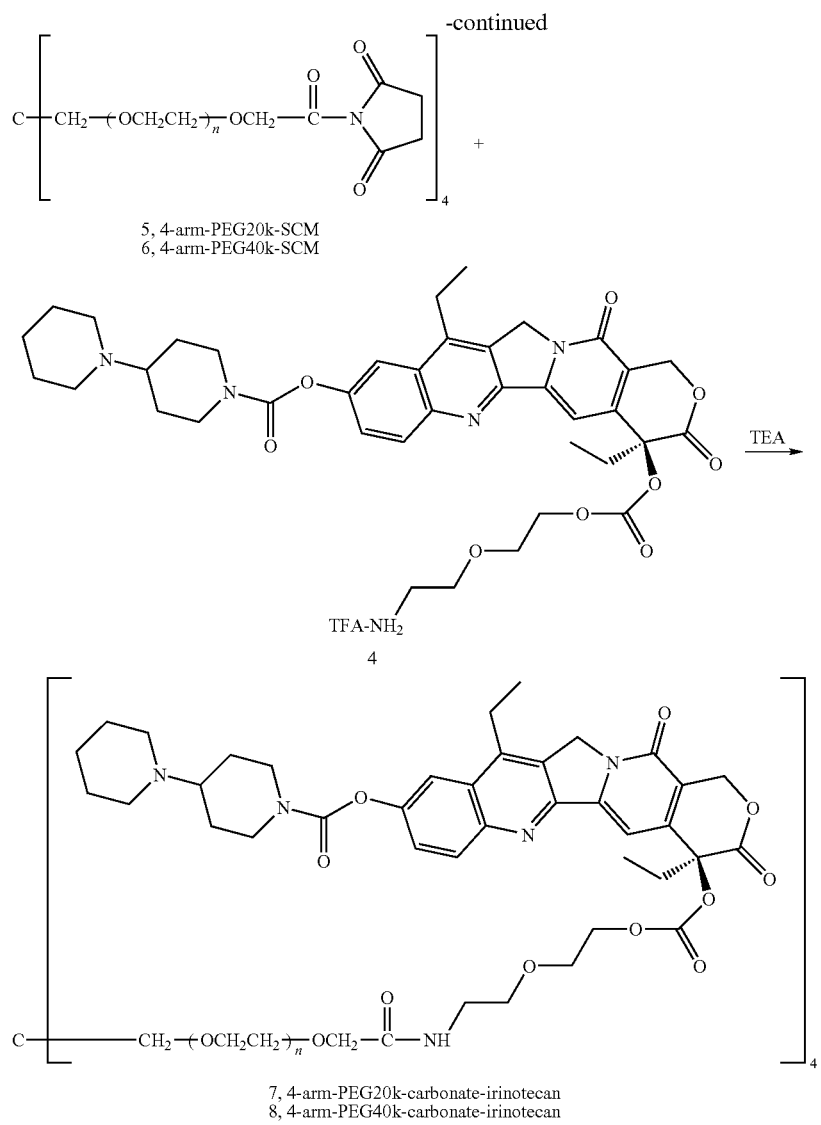

5, 4-arm-PEG20k-SCM
6, 4-arm-PEG40k-SCM 7, 4-arm-PEG20k-carbonate-irinotecan
8, 4-arm-PEG40k-carbonate-irinotecan A. 2-(2-t-Boc-aminoethoxy)ethanol (1)

2-(2-Aminoethoxy)ethanol (10.5 g, 0.1 mol) and NaHCO$_3$ (12.6 g, 0.15 mol) were added to 100 mL CH$_2$Cl$_2$ and 100 mL H$_2$O. The solution was stirred at RT for 10 minutes, then di-tert-butyl dicarbonate (21.8 g, 0.1 mol) was added. The resulting solution was stirred at RT overnight, then extracted with CH$_2$Cl$_2$ (3×100 mL). The organic phases were combined and dried over anhydrous sodium sulfate and evaporated under vacuum. The residue was subjected to silica gel column chromatography (CH$_2$Cl$_2$:CH$_3$OH=50:1~10:1) to afford 2-(2-t-Boc-aminoethoxy)ethanol (1) (16.0 g, 78 mmol, yield 78%)

B. 2-(2-t-Boc-aminoethoxy)ethoxycarbonyl-Irinotecan (2)

2-(2-t-Boc-aminoethoxy)ethanol (1) (12.3 g, 60 mmol) and 4-dimethylaminopyridine (DMAP) (14.6 g, 120 mmol) were dissolved in 200 ml anhydrous CH$_2$Cl$_2$. Triphosgene (5.91 g, 20 mmol) was added to the solution while stirring at room temperature. After 20 minutes, the solution was added to a solution of irinotecan (6.0 g, 10.2 mmol) and DMAP (12.2 g, 100 mmol) in anhydrous CH$_2$Cl$_2$ (200 mL). The reaction was stirred at RT for 2 hrs, then washed with HCl solution (pH=3, 2 L) to remove DMAP. The organic phases were combined and dried over anhydrous sodium sulfate. The dried solution was evaporated under vacuum and subjected to silica gel column chromatography (CH$_2$Cl$_2$:CH$_3$OH=40:1~10:1) to afford 2-(2-t-Boc-aminoethoxy)ethoxycarbonyl-irinotecan (2) (4.9 g, 6.0 mmol, yield 59%).

C. 2-(2-aminoethoxy)ethoxycarbonyl-irinotecan TFA salt (3)

2-(2-t-Boc-aminoethoxy)ethoxycarbonyl-irinotecan (2) (4.7 g, 5.75 mmol) was dissolved in 60 mL CH$_2$Cl$_2$, and trifluoroacetic acid (TFA) (20 mL) was added at RT. The reaction solution was stirred for 2 hours. The solvents were removed under vacuum and the residue was added to ethyl ether and filtered to give a yellow solid as product 3 (4.3 g, yield 90%).

D. 4-arm-PEG$_{20k}$-carbonate-inotecan (4)

4-arm-PEG$_{20k}$-SCM (16.0 g) was dissolved in 200 mL CH$_2$Cl$_2$. 2-(2-aminoethoxy)ethoxycarbonyl-irinotecan TFA salt (3) (2.85 g, 3.44 mmol) was dissolved in 12 mL DMF and treated with 0.6 mL TEA, then added to a solution of 4-arm-PEG$_{20k}$-SCM. The reaction was stirred at RT for 12 hrs then precipitated in Et$_2$O to yield a solid product, which was dissolved in 500 mL IPA at 50° C. The solution was cooled to RT and the resulting precipitate collected by filtration to give 4-arm-PEG$_{20k}$-glycine-irinotecan (4) (16.2 g, drug content 7.5% based on HPLC analysis). Yield: 60%.

E. 4-arm-PEG$_{40k}$-carbonate-irinotecan (5)

4-arm-PEG$_{40k}$-SCM (32.0 g) was dissolved in 400 mL CH$_2$Cl$_2$. 2-(2-aminoethoxy)ethoxycarbonyl-irinotecan TFA salt (3) (2.85 g, 3.44 mmol) was dissolved in 12 mL DMF and treated with 0.6 mL TEA, then added to the solution of 4-arm-PEG$_{40k}$-SCM. The reaction was stirred at RT for 12 hrs and then precipitated in Et$_2$O to get solid product, which was dissolved in 1000 mL isopropyl alcohol (IPA) at 50° C. The solution was cooled to RT and the precipitate collected by filtration to gave 4-arm-PEG$_{40k}$-glycine-irinotecan (4) (g, drug content 3.7% based on HPLC analysis). Yield: 59%.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A multi-arm polymer prodrug having the structure:

$$R\!-\!(\!O\!-\!(CH_2CH_2O)_n\!-\!X\!-\!D\,)_q$$

wherein:
R is an organic radical possessing from 3 to 25 carbon atoms;
X is a spacer having an atom length of from 4 atoms to 50 atoms possessing the structure Y—Z, where Y has the structure —(CH$_2$)$_a$—C(O)NH—(CH$_2$)$_b$—(CH$_2$CH$_2$O)$_c$— and Z is either —C(O)—O— or —O—C(O)—O—; where
a is selected from 1, 2, 3, and 4;
b is selected from 1, 2, 3, and 4;
c ranges from 0 to 10;
n ranges from 5 to 400;
D is a camptothecin attached at its 10-, 11- or 20-ring position; and
q has a value from 3 to 25.

2. The multi-arm polymer prodrug of claim 1, wherein R possesses a number of carbon atoms selected from the group consisting of 3, 4, 5, 6, 7, 8, 9, and 10.

3. The multi-arm polymer prodrug of claim 1, wherein R, taken together with the adjacent oxygen atom to form R(—O—)$_q$, is a residue of glycerol, trimethylolpropane, pentaerythritol, sorbitol, or glycerol oligomers after removal of "q" hydroxyl protons.

4. The multi-armed polymer prodrug of claim 1, where R(—O—)$_q$ is selected from:

(i)

m = 0-5

(ii)

(iii)

(iv)

(v)

5. The multi-arm polymer prodrug of claim 1, having an overall nominal average molecular weight from 800 to 60,000 daltons.

6. The multi-arm polymer prodrug of claim 5, wherein the nominal average molecular weight of —(CH$_2$CH$_2$O)$_n$— in each of "q" arms is selected from 200, 250, 300, 400, 500, 600, 700, 800, 900, 1000, 1500, 2000, 3000, 4000, 5000, 6000, 7000, 7500, 8000, 9000, 10000, 12,000, 15000, 17,500, 18,000, 19,000, and 20,000 daltons.

7. The multi-arm polymer prodrug of claim 1, wherein the nominal average molecular weight of —(CH$_2$CH$_2$O)$_n$— in each of "q" arms ranges from 500 to 20,000 daltons.

8. The multi-arm polymer prodrug of claim 1, wherein the value of q is selected from the group consisting of 3, 4, 5, 6, 7, 8, 9, and 10.

9. The multi-arm polymer prodrug of claim 1, wherein each of said "q" polymer arms is the same.

10. The multi-arm polymer prodrug of claim 1, wherein X has a length of from 5 atoms to 25 atoms.

11. The multi-arm polymer prodrug of claim 1, where Y has the structure: —CH$_2$C(O)NHCH$_2$(CH$_2$CH$_2$O)$_{0-10}$—.

12. The multi-arm polymer prodrug of claim 1, wherein X is either —CH$_2$—C(O)—NH—CH$_2$—C(O)O— or —CH$_2$—C(O)—NH—(CH$_2$CH$_2$O)$_2$—C(O)—O—.

13. The multi-arm polymer prodrug of claim 1, wherein D is a camptothecin compound having the structure:

VII wherein $R_1$-$R_5$ are each independently selected from the group consisting of hydrogen; halo; acyl; alkyl (e.g., C1-C6 alkyl); substituted alkyl; alkoxy; substituted alkoxy; alkenyl; alkynyl; cycloalkyl; hydroxyl; cyano; nitro; azido; amido; hydrazine; amino; substituted amino; hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy;

$R_6$ is H or OR', wherein R' is alkyl, alkenyl, cycloalkyl, haloalkyl, or hydroxyalkyl; and L is the site of attachment.

14. The multi-arm polymer prodrug of claim 1, where D is SN-38.

15. The multi-arm polymer prodrug of claim 12, having the structure:

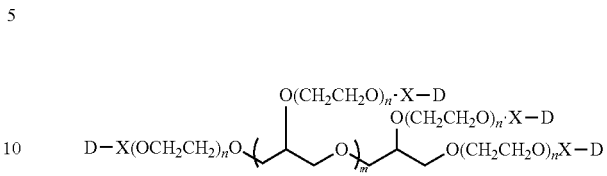

where m is an integer ranging from 0 to 5, and D is SN-38.

16. The multi-arm polymer prodrug of claim 15, wherein —X-D corresponds to —CH$_2$—C(O)—NH—CH$_2$—C(O)O-SN-38.

17. A pharmaceutical composition comprising a multi-arm polymer prodrug of claim 1.

* * * * *